(12) United States Patent
Maeda et al.

(10) Patent No.: US 7,006,681 B2
(45) Date of Patent: Feb. 28, 2006

(54) INSPECTION METHOD OF ELECTRICAL PART, INSPECTION APPARATUS OF ELECTRIC JUNCTION BOX AND INSPECTION APPARATUS OF TERMINAL FITTINGS

(75) Inventors: Tatsuya Maeda, Shizuoka (JP); Shigenori Miyawaki, Shizuoka (JP)

(73) Assignee: Yazaki Corporation, Tokyo (JP)

( * ) Notice: Subject to any disclaimer, the term of this patent is extended or adjusted under 35 U.S.C. 154(b) by 740 days.

(21) Appl. No.: 09/963,710

(22) Filed: Sep. 27, 2001

(65) Prior Publication Data

US 2002/0036512 A1    Mar. 28, 2002

(30) Foreign Application Priority Data

Sep. 28, 2000 (JP) .............................. 2000-296334
Aug. 23, 2001 (JP) .............................. 2001-253350

(51) Int. Cl.
*G06K 9/00* (2006.01)
(52) U.S. Cl. ..................................................... 382/141
(58) Field of Classification Search ................ 382/141, 382/143–152; 348/86, 87, 125, 126, 94; 356/237.1, 237.4, 237.5; 378/98.2
See application file for complete search history.

(56) References Cited

U.S. PATENT DOCUMENTS

| | | | | |
|---|---|---|---|---|
| 4,809,308 A | * | 2/1989 | Adams et al. | .............. 378/98.2 |
| 5,369,430 A | * | 11/1994 | Kitamura | ...................... 348/94 |
| 5,495,424 A | | 2/1996 | Tokura | |
| 5,568,563 A | * | 10/1996 | Tanaka et al. | ............... 382/144 |
| 6,577,757 B1 | * | 6/2003 | DeYong et al. | ............. 382/149 |
| 6,748,104 B1 | * | 6/2004 | Bachelder et al. | .......... 382/151 |

FOREIGN PATENT DOCUMENTS

| | | |
|---|---|---|
| EP | 0 500 315 A | 8/2002 |
| FR | 2 553 914 A | 4/1985 |

OTHER PUBLICATIONS

Patent Abstracts of Japan, vol. 2000, No. May 11, 2001 (corresponds to JP 2001 197643 A).
Patent Abstracts of Japan, vol. 2000, No. 03, Mar. 30, 2000 (corresponds to JP 11 351839 A).
English translation of Chinese Office Action having Date of Notification of Aug. 12, 2005.

* cited by examiner

Primary Examiner—Vikkram Bali
(74) Attorney, Agent, or Firm—Armstrong, Kratz, Quintos, Hanson & Brooks, LLP.

(57) ABSTRACT

An inspection apparatus of an electric junction box is provided, by which improper mounting of electric parts can be detected. The inspection apparatus 1 has a CCD camera 5, an image-processing device 7 and a control device 8. The CCD camera picks up images of fuse 14 in the electric junction box 12 as a subject of the inspection. The image-processing device 7 stores an image consulting data 60. The image consulting data 60 includes a plurality of images of each fuse 14 having the same item symbol with regard to every item symbol, the fuses 14 being used in the electric junction box 12. The control device 8 stores normal data indicating the proper item symbol of the fuse 14 to be mounted on a corresponding mount 13. The image-processing device 7 extracts the image most analogous to the image picked up by the CCD camera 5 from the images in the image consulting data. The control device 8 judge the quality of the item symbol of the fuse 14 having the most analogous image on the basis of the normal data.

13 Claims, 20 Drawing Sheets

FIG. 2

IMAGE CONSULTING DATA

| STORED IMAGE / ITEM SYMBOL | No 1 | No 2 | No 3 | | No 3 |
|---|---|---|---|---|---|
| A ITEM SYMBOL | 1 0 A | A 0 1 | 1 0 A | | 1 0 A |
| B ITEM SYMBOL | 2 0 A | A 0 2 | 2 0 A | | 2 0 A |
| C ITEM SYMBOL | 3 0 A | A 0 3 | 3 0 A | | 3 0 A |
| N ITEM SYMBOL | | | | | |

FIG. 3

NORMAL DATA

| SECTION TO BE INSPECTED | ITEM SYMBOL |
|---|---|
| R 0 | A ITEM SYMBOL |
| R 1 | B ITEM SYMBOL |
| R 2 | C ITEM SYMBOL |
| R 3 | A ITEM SYMBOL |
| R N | |

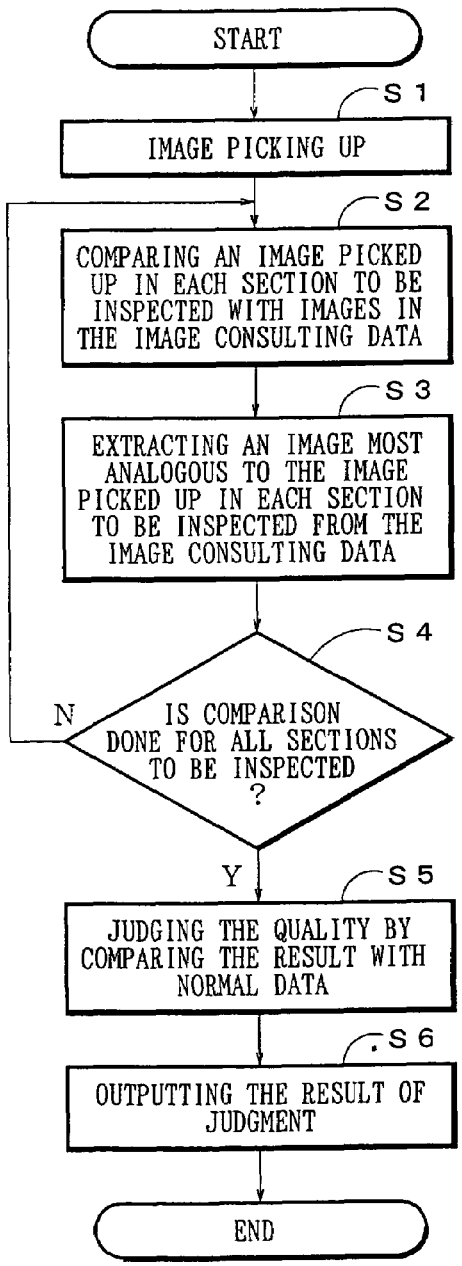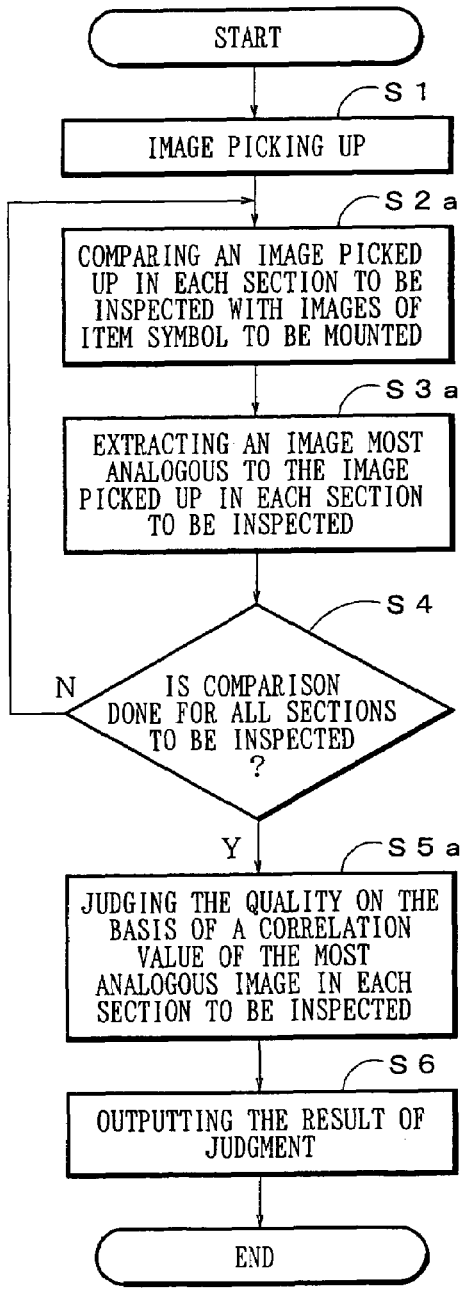

FIG. 9

| STORED IMAGE \ PORTION OF PRESSURE-WELDING TERMINAL FOR JB | No 1 | No 2 | No 3 | | NoN |
|---|---|---|---|---|---|
| ELECTRIC CONTACT IN ODD LINE | | | | | |
| CAULKING PIECE IN ODD LINE | | | | | |
| PRESSURE-WELDING PART IN ODD LINE | | | | | |
| ELECTRIC CONTACT IN EVEN LINE | | | | | |
| CAULKING PIECE IN EVEN LINE | | | | | |
| PRESSURE-WELDING PART IN EVEN LINE | | | | | |

IMAGE CONSULTING DATA

| SECTION TO BE INSPECTED | PORTION OF PRESSURE-WELDING TERMINAL FOR JB |
|---|---|
| Ra0 | ELECTRIC CONTACT IN ODD LINE |
| Ra1 | CAULKING PIECE IN ODD LINE |
| Ra2 | PRESSURE-WELDING PART IN ODD LINE |
| Ra(N-2) | ELECTRIC CONTACT IN ODD LINE |
| Ra(N-1) | CAULKING PIECE IN ODD LINE |
| RaN | PRESSURE-WELDING PART IN ODD LINE |

| SECTION TO BE INSPECTED | PORTION OF PRESSURE-WELDING TERMINAL FOR JB |
|---|---|
| Rb0 | PRESSURE-WELDING PART IN EVEN LINE |
| Rb1 | CAULKING PIECE IN EVEN LINE |
| Rb2 | ELECTRIC CONTACT IN EVEN LINE |
| Rb(N-2) | PRESSURE-WELDING PART IN EVEN LINE |
| Rb(N-1) | CAULKING PIECE IN EVEN LINE |
| RbN | ELECTRIC CONTACT IN EVEN LINE |

FIG. 14

| STORED IMAGE / PORTION OF PRESSURE-WELDING TERMINAL FOR JB | No1 | No2 | No3 | | NoN |
|---|---|---|---|---|---|
| CAULKING PIECE IN ODD LINE | ▯ | ▯ | ▯ | | ▯ |
| PRESSURE-WELDING PART IN ODD LINE | ⊟ | ⊟ | ⊟ | | ⊟ |
| CAULKING PIECE IN EVEN LINE | ▯ | ▯ | ▯ | | ▯ |
| PRESSURE-WELDING PART IN EVEN LINE | ⊟ | ⊟ | ⊟ | | ⊟ |

SECOND IMAGE CONSULTING DATA 2b

FIG. 15

| SECTION TO BE INSPECTED | PORTION OF PRESSURE-WELDING TERMINAL FOR JB |
|---|---|
| Rc0 | CAULKING PIECE IN ODD LINE |
| Rc1 | PRESSURE-WELDING PART IN ODD LINE |
| Rc(N−1) | CAULKING PIECE IN ODD LINE |
| RcN | PRESSURE-WELDING PART IN ODD LINE |

FIG. 16

| SECTION TO BE INSPECTED | PORTION OF PRESSURE-WELDING TERMINAL FOR JB |
|---|---|
| Rd0 | PRESSURE-WELDING PART IN EVEN LINE |
| Rd1 | CAULKING PIECE IN EVEN LINE |
| Rd(N−1) | PRESSURE-WELDING PART IN EVEN LINE |
| RdN | CAULKING PIECE IN EVEN LINE |

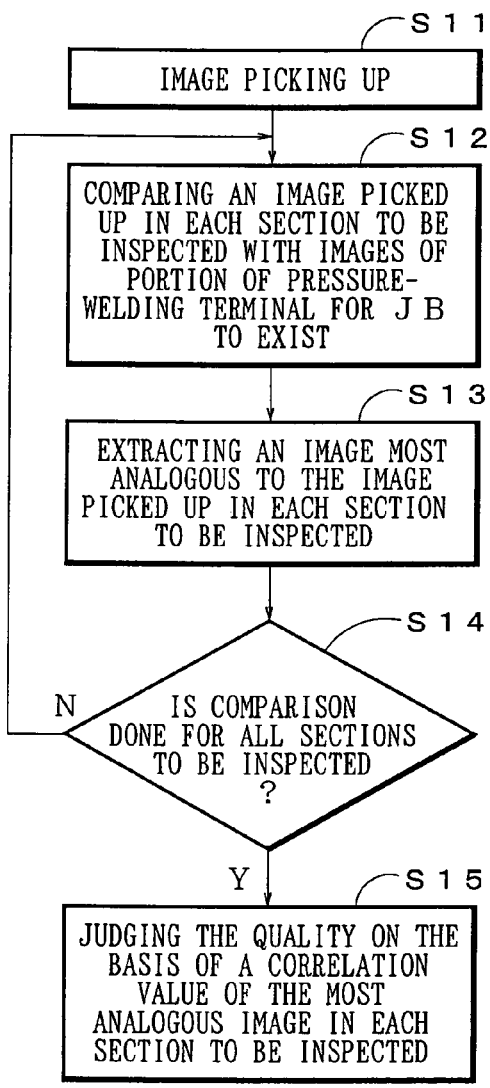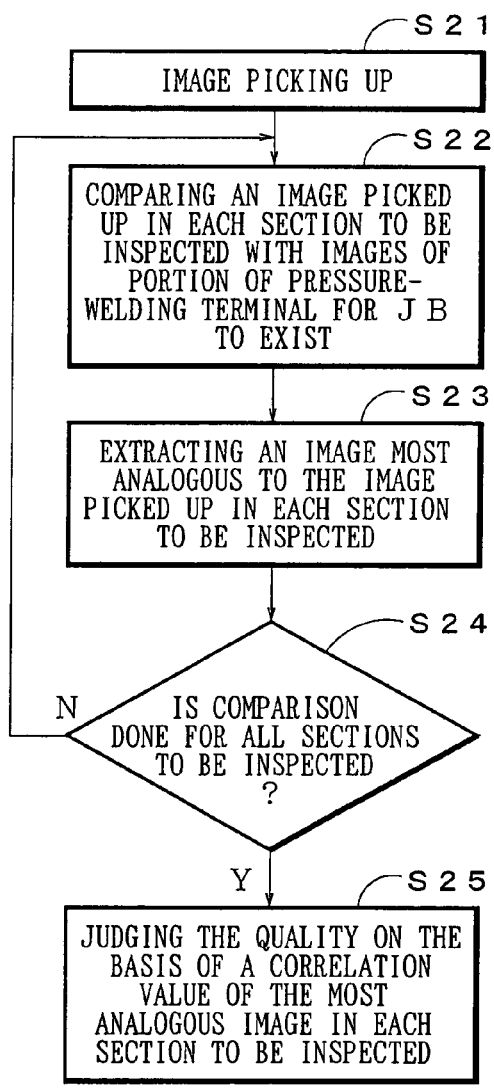

INSPECTION METHOD OF ELECTRICAL PART, INSPECTION APPARATUS OF ELECTRIC JUNCTION BOX AND INSPECTION APPARATUS OF TERMINAL FITTINGS

BACKGROUND OF THE INVENTION (1) Field of the Invention

The present invention relates to an inspection method of an electric part such as a fuse and terminal fittings, to an inspection apparatus of an electric junction box for inspecting whether or not an electric part such as a fuse having an item symbol, which should be mounted on a mount, is mounted, and to an inspection apparatus of a terminal fittings for inspecting the quality of the terminal fittings mounted on an insulator.

(2) Description of the Related Art

Generally, on a motor vehicle as a mobile unit, there are mounted various electronic equipment, for example, lamps such as headlamps and tail lamps, and motors such as a starter motor and a motor for an air-conditioner.

In order to supply the electric power to the various electronic equipment, there are disposed junction blocks at suitable positions in the motor vehicle. In the junction block, wiring boards having printed-wiring boards and bus bars are laminated, into which various electric circuit units are integrated, thereby the junction block is constituted.

Since the junction block may have fuses, relays and bus bars, the junction block may be called as a fuse block, relay box, or an electric junction box as the general term. In this specification, the aforementioned fuse block, relay box and junction block are hereinafter called an electric junction box.

In such a junction box, various electric parts such as fuses, relays, diodes and fusible links are mounted. Each terminal of these electric parts is connected to the wiring board. The junction box electrically connects wires, which are connected to the power sources or loads, to the various electric parts in accordance with a predetermined pattern.

For example, a fuse, which is one of the aforementioned electric parts, has a plurality of item symbols having different capacity. On the outer surface of the fuse, there is shown a mark (for example, 10A and 20A) according to the permissible current. Generally, in the electric junction box, there are mounted fuses having a plurality of item symbols.

When the electric junction box, in which fuses having a plurality of item symbols are mounted, is assembled, a worker mounts each fuse having a required permissible current on a corresponding predetermined position in the electric junction box. Thereafter, whether or not each fuse is properly mounted on the corresponding position is judged by carrying out a continuity test for the electric junction box together with the visual inspection thereof.

In addition, the motor vehicle has a wiring harness for supplying the electric power and control signals to the various electronic equipment mentioned above. The wiring harness comprises a plurality of electric wires and connectors, which are connected to ends of the wires. The wire is so-called a coated wire having an electrically conductive core and an electrically insulating coating portion, which coats the core. The connector has a terminal fittings as an electric part and an insulating connector housing.

The terminal fittings is made by bending an electrically conductive sheet metal and has a pressure-welding part to be pressure-welded to the wire and a caulking piece for caulking the wire. The pressure-welding part has a pair of blades for pressure welding. A pair of the blades cut the coating portion of the wire so as to come in contact with the core when the wire is press-fit between a pair of the blades, thus the pressure-welding part is pressure-welded to the wire. The caulking piece caulks the wire by being bent. The connector housing has a plurality of mounts on which the terminal fittings are mounted. The connector housing mounts the terminal fittings thereon by mounting the terminal fittings on the mounts thereof.

After the terminal fittings are mounted on the mounts of the connector housing, the wire is pressure-welded to the pressure-welding part of the terminal fittings and the caulking piece is bent, thus the terminal fittings is fixed to the wire. In this way, the wiring harness is assembled. When the wiring harness is assembled, the quality of the pressure-welding part and the caulking piece of the terminal fittings, which is mounted on the connector housing, have so far been inspected by a known appearance inspection apparatus. Also, the quality of the pressure-welding part and the caulking piece of the terminal fittings, to which the wire is pressure-welded, have so far been inspected by a known appearance inspection apparatus.

The appearance inspection apparatus mentioned above stores one image of a non-defective terminal fittings in advance and another image of a non-defective terminal fittings to which a wire is pressure-welded in advance. Then, after obtaining an image of the terminal fittings mounted on the connector housing to be inspected and an image of the terminal fittings to which the wire is pressure-welded, the quality of the terminal fittings and that of the pressure-welding state of the wire have so far been judged by comparing these images with the images of the non-defective.

In the aforementioned conventional assembling method of the electric junction box, since a worker selects a required fuse and mounts it on a corresponding position of the electric junction box, there is a possibility that a fuse of improper permissible current is mounted on the corresponding position. Furthermore, since a worker confirms the permissible current of the fuse mounted on the position by the visual inspection, there is a possibility that a fuse of improper permissible current is still mounted on the corresponding position.

In addition, since the terminal fittings is made of sheet metal, if the brightness of the lighting or the positional relation between the terminal fittings and the lighting is changed, the image of the terminal fittings mounted on the connector housing changes. Therefore, when the quality of the terminal fittings is judged by using the appearance inspection apparatus mentioned above, mistake in the judgement, such as judging a non-defective terminal fittings to be defective and judging a defective terminal fittings to be non-defective, can often arise. Therefore, so far it has been difficult to securely judge the quality of the terminal fittings.

As described above, it has been difficult to securely judge the quality of a fuse or a terminal fittings with the conventional inspection method.

SUMMARY OF THE INVENTION

Therefore, a first objective of the present invention is to provide an inspection method of an electric part, by which the quality of the electric part can be securely judged. A second objective of the present invention is to provide an inspection apparatus of an electric junction box, by which a mounting of an improper electric part in the electric junction box can be securely detected. A third objective of the present invention is to provide an inspection apparatus of a terminal fittings, by which the quality of the terminal fittings can be securely judged.

In order to attain the first objective, the present invention is to provide an inspection method of an electric part comprising the steps of:

storing a plurality of images of a non-defective electric part in advance; and judging whether or not an electric part to be inspected is non-defective on the basis of an image of the electric part to be inspected and a plurality of the images of a non-defective electric part.

With the construction described above, since a plurality of the images of a non-defective part are stored in advance, an image analogous to the image of the part to be inspected can be included in the stored images of a non-defective part with high possibility. Therefore, the image of the part to be inspected can very well coincide with the image most analogous to the image thereof out of the stored images of a non-defective part. Therefore, a mistake in judgement of the quality of the part can be prevented.

In order to attain the first objective, the present invention is to provide an inspection method of an electric part comprising the steps of:

storing a plurality of images of a non-defective electric part in advance;

comparing an image of an electric part to be inspected and a plurality of the images of a non-defective electric part;

extracting an image most analogous to the image of an electric part to be inspected from a plurality of the images of a non-defective electric part; and judging whether or not the electric part to be inspected is non-defective on the basis of the most analogous image and the image of the electric part to be inspected.

With the construction described above, since a plurality of the images of a non-defective part are stored in advance, an image analogous to the image of the part to be inspected can be included in the stored images of a non-defective part with high possibility. Therefore, the image of the part to be inspected can very well coincide with the image most analogous to the image thereof out of the stored images of a non-defective part. In addition, the quality of the part is judged on the basis of the most analogous image and the image of the part to be inspected. Therefore, a mistake in judgement of the quality of the part can be prevented.

In order to attain the second objective, the present invention is to provide an inspection apparatus of an electric junction box having a plurality of mounts on which electric parts are mounted, for inspecting mounting state of the electric parts, said each electric part having a different mark on an outer surface thereof depending upon an item symbol thereof, the inspection apparatus comprising:

image pickup means for picking up an image including said mark of the electric part mounted on the mount;

extraction means for (1) storing image consulting data containing a plurality of images including said marks of the electric parts of all the item symbols to be mounted in the electric junction box as a subject of the inspection and normal data indicating the proper item symbols of the electric parts mounted on the corresponding mounts, and for (2) comparing the image including said mark of the electric part mounted on the mount picked up by the image pickup means and the image in the image consulting data, and for (3) extracting the item symbol of the electric part having the most analogous image from the images in the image consulting data; and judgment means for judging the quality of the mounting state of the electric parts on the mount by comparing the item symbol of the electric part having the most analogous image and said normal data.

With the construction described above, the images of the item symbol of the electric part to be mounted in the electric junction box is stored in advance, and in addition, a plurality of images for each item symbol are stored. The most analogous image to the image picked up by the image pickup means is extracted out of these stored images.

Therefore, an image analogous to the image of the electric part, which is picked up by the image pickup means, is included in the image consulting data with high possibility. That is, the degree of coincidence between the image picked up by the image pickup means and the most analogous image out of the stored images becomes high. Therefore, by storing a plurality of images of the electric part having the same item symbol in the image consulting data, the item symbol of the electric part mounted on the mount can be distinguished.

In addition, the item symbol of the electric part having the most analogous image and said normal data are compared so as to judge the quality of the mounting state of the electric parts on the mount. Therefore, an improper mounting, that is, that an electric part having an improper item symbol is mounted on the mount can be securely detected.

Preferably, the image is a digital information, in which an optical power is indicated with a plurality of grades thereof, the extraction means compares the image including said mark of the electric part mounted on the mount in the electric junction box as a subject of the inspection and the image in the image consulting data by a method of normalization correlation so that the image having the highest correlation value obtained by the method of normalization correlation out of the images is set up to be said most analogous image, and the judgment means judges the quality of the mounting state of the electric parts on the mount by comparing the item symbol of the electric part of the image having the highest correlation value and said normal data.

With the construction described above, the method of normalization correlation is employed when the image most analogous to the image picked up by the image pickup means is extracted. In the method of normalization correlation, two images subjected to the comparison are relatively moved, enlarged and reduced so as to adjust their size (that is, to normalize) followed by carrying out a correlation, thereby computing a correlation value indicating the degree of coincidence between the two images.

Thus, since the method of normalization correlation is employed, the two images, in each of which an optical power is indicated with a plurality of grades, are compared (matched) with each other. On the other hand, the images having the same item symbol have about the same variation in the optical intensity. Therefore, the degree of coincidence between the images having the same item symbol becomes higher compared to a case, in which images recorded in a binary condition are compared with each other.

Therefore, the degree of coincidence between the image picked up by the image pickup means and the most analogous image out of these stored images becomes higher, thereby the item symbol of the electric part mounted on the mount can be more securely distinguished.

In order to attain the second objective, the present invention is to provide an inspection apparatus of an electric junction box having a plurality of mounts on which electric parts are mounted, for inspecting mounting state of the electric parts, said each electric part having a different mark on an outer surface thereof depending upon an item symbol thereof, the inspection apparatus comprising:

image pickup means for picking up an image including said mark of the electric part mounted on the mount;

extraction means for (1) storing image consulting data containing a plurality of images including said marks of the electric parts of all the item symbols to be mounted in the electric junction box as a subject of the inspection, and for (2) comparing the image including said mark of the electric part mounted on the mount picked up by the image pickup means and the image of the electric part having the proper item symbol to be mounted in the image consulting data by a method of normalization correlation, and for (3) extracting the highest correlation value out of the correlation values obtained by the method of normalization correlation; and judgment means for judging the quality of the mounting state of the electric parts on the mount on the basis of the highest correlation value.

With the construction described above, the image picked up by the image pickup means and the image of the electric part having the proper item symbol to be mounted are compared by a method of normalization correlation. Then, whether or not the electric part having a proper item symbol is mounted on the mount is judged on the basis of the correlation value obtained by the method of normalization correlation.

The images of the electric part having the item symbol to be mounted in the electric junction box are stored in advance, and in addition, a plurality of the images of the electric part having the same item symbol are stored. Therefore, an image analogous to the image of the electric part, which is picked up by the image pickup means, is included in the image consulting data with high possibility. That is, the degree of coincidence between the image picked up by the image pickup means and the most analogous image out of the images in the image consulting data becomes high. Therefore, whether or not the electric part having the proper item symbol is mounted on the mount can be securely judged.

Preferably, the judgment means adds the image including said mark of the electric part properly mounted on the mount, out of the electric parts judged improperly mounted on the mount, to the image consulting data.

With the construction described above, the images of the electric part judged to be improperly mounted on the mount are added to the image consulting data. Therefore, an image analogous to the image of the electric part, which is picked up by the image pickup means, is included in the image consulting data with higher possibility.

Therefore, the degree of coincidence between the image picked up by the image pickup means and the most analogous image out of the images in the image consulting data becomes higher, thereby the item symbol of the electric part mounted on the mount can be more securely distinguished.

In order to attain the third objective, the present invention is to provide an inspection apparatus of a terminal fittings for inspecting mounting state of the terminal fittings on an insulator, said terminal fittings being mounted on the insulator and an electric wire being pressure-welded to the terminal fittings, the inspection apparatus comprising:

image pickup means for picking up an image of the terminal fittings mounted on the insulator;

extraction means for (1) storing image consulting data containing a plurality of images of a non-defective terminal fittings mounted on the insulator, and for (2) comparing the image of the terminal fittings picked up by the image pickup means and a plurality of the images of a non-defective terminal fittings in the image consulting data, and for (3) extracting an image most analogous to the image of the terminal fittings picked up by the image pickup means from the images in the image consulting data; and judgment means for judging the quality of the mounting state of the terminal fittings on the insulator by comparing the most analogous image and the image of the terminal fittings picked up by the image pickup means.

With the construction described above, since a plurality of the images of a terminal fittings to be mounted on the insulator are stored in advance. Out of these images, an image most analogous to the image picked up by the image pickup means is extracted.

Therefore, an image analogous to the image of the terminal fittings picked up by the image pickup means can be included in the image consulting data with high possibility. Therefore, the image of the terminal fittings picked up by the image pickup means can very well coincide with the image most analogous to the image thereof out of the stored images in the image consulting data. In addition, the quality of the mounting state of the terminal fittings on the insulator is judged by comparing the most analogous image and the image picked up by the image pickup means. Therefore, a mistake in detection such as judging a non-defective part to be a defective part can be prevented.

Preferably, the image is a digital information, in which an optical power is indicated with a plurality of grades thereof, the extraction means compares the image of the terminal fittings picked up by the image pickup means and a plurality of the image in the image consulting data by a method of normalization correlation so that the image having the highest correlation value obtained by the method of normalization correlation out of the images is set up to be said most analogous image, and the judgment means judges the quality of the mounting state of the terminal fittings on the insulator to be good when the correlation value is equal to or higher than a predetermined threshold while judges the quality of the mounting state to be no good when the correlation value is lower than the predetermined threshold.

In the construction described above, the method of normalization correlation is employed. That is, two images to be compared are relatively moved, enlarged and reduced so as to match their size with each other (i.e. to carry out the normalization). After this normalization, the correlation is carried out so as to calculate the correlation value indicating the degree of coincidence between the two images.

Since the normalization correlation method is carried out, the two images, in which an optical power is indicated with a plurality of grades, are matched with each other. The images of the same terminal fittings have about the same variation in the optical intensity with each other. Therefore, the degree of coincidence between the images of the same terminal fittings becomes higher compared to a case, in which images recorded in a binary condition are compared with each other. Consequently, since the image picked up by the image pickup means can very well coincides with the most analogous image, a mistake in detection such as judging a non-defective part to be a defective part can be prevented.

In order to attain the third objective, the present invention is to provide an inspection apparatus of a terminal fittings for inspecting pressure-welding state of an electric wire to the terminal fittings, said terminal fittings being mounted on an insulator and the electric wire being pressure-welded to the terminal fittings, the inspection apparatus comprising:

image pickup means for picking up an image of the terminal fittings, to which the electric wire is pressure-welded, mounted on the insulator;

second extraction means for (1) storing second image consulting data containing a plurality of images of a non-defective terminal fittings, to which the electric wire is pressure-welded, mounted on the insulator, and for (2) comparing the image of the terminal fittings, to which the electric wire is pressure-welded, picked up by the image pickup means and a plurality of images of a non-defective terminal fittings, to which the electric wire is pressure-welded, in the second image consulting data, and for (3) extracting an image most analogous to the image of the terminal fittings, to which the electric wire is pressure-welded, picked up by the image pickup means from the images in the second image consulting data; and second judgment means for judging the quality of the pressure-welding state of the electric wire to the terminal fittings, to which the electric wire is pressure-welded, mounted on the insulator by comparing the most analogous image and the image of the terminal fittings, to which the electric wire is pressure-welded, mounted on the insulator picked up by the image pickup means.

With the construction described above, since a plurality of the images of a terminal fittings, to which the wire is pressure-welded, mounted on the insulator are stored in advance. Out of these images, an image most analogous to the image picked up by the image pickup means is extracted.

Therefore, an image analogous to the image of the terminal fittings picked up by the image pickup means can be included in the second image consulting data with high possibility. Therefore, the image of the terminal fittings picked up by the image pickup means can very well coincide with the image most analogous to the image thereof out of the stored images in the second image consulting data. In addition, the quality of the pressure-welding state of the wire to terminal fittings mounted on the insulator is judged by comparing the most analogous image and the image picked up by the image pickup means. Therefore, a mistake in detection such as judging a non-defective part to be a defective part can be prevented.

Preferably, the image is a digital information, in which an optical power is indicated with a plurality of grades thereof, the second extraction means compares the image of the terminal fittings, to which the electric wire is pressure-welded, picked up by the image pickup means and a plurality of the images in the second image consulting data by a method of normalization correlation so that the image having the highest correlation value obtained by the method of normalization correlation out of the images is set up to be said most analogous image, and the second judgment means judges the quality of the pressure-welding state of the electric wire to the terminal fittings to be good when the correlation value is equal to or higher than a predetermined threshold while judges the quality of the pressure-welding state to be no good when the correlation value is lower than the predetermined threshold.

In the construction described above, the method of normalization correlation is employed. That is, two images to be compared are relatively moved, enlarged and reduced so as to match their size with each other (i.e. to carry out the normalization). After this normalization, the correlation is carried out so as to calculate the correlation value indicating the degree of coincidence between the two images.

Since the normalization correlation method is carried out, the two images, in which an optical power is indicated with a plurality of grades, are matched with each other. The images of the same terminal fittings have about the same variation in the optical intensity with each other. Therefore, the degree of coincidence between the images of the same terminal fittings becomes higher compared to a case, in which images recorded in a binary condition are compared with each other. Consequently, since the image picked up by the image pickup means can very well coincides with the most analogous image, a mistake in detection such as judging a non-defective part to be a defective part can be prevented.

In order to attain the third objective, the present invention is to provide an inspection apparatus of a terminal fittings for inspecting mounting state of the terminal fittings on an insulator and pressure-welding state of an electric wire, said terminal fittings being mounted on the insulator and the electric wire being pressure-welded to the terminal fittings, the inspection apparatus comprising:

image pickup means for picking up an image of the terminal fittings mounted on the insulator;

extraction means for (1) storing image consulting data containing a plurality of images of a non-defective terminal fittings mounted on the insulator, and for (2) comparing the image of the terminal fittings picked up by the image pickup means and a plurality of the images of a non-defective terminal fittings in the image consulting data, and for (3) extracting an image most analogous to the image of the terminal fittings picked up by the image pickup means from the images in the image consulting data;

judgment means for judging the quality of the mounting state of the terminal fittings on the insulator by comparing the most analogous image and the image of the terminal fittings picked up by the image pickup means;

second extraction means for (1) storing second image consulting data containing a plurality of images of a non-defective terminal fittings, to which the electric wire is pressure-welded, mounted on the insulator, and for (2) comparing the image of the terminal fittings, to which the electric wire is pressure-welded, picked up by the image pickup means and a plurality of images of a non-defective terminal fittings, to which the electric wire is pressure-welded, in the second image consulting data, and for (3) extracting an image most analogous to the image of the terminal fittings, to which the electric wire is pressure-welded, picked up by the image pickup means from the images in the second image consulting data; and second judgment means for judging the quality of the pressure-welding state of the electric wire to the terminal fittings, to which the electric wire is pressure-welded, mounted on the insulator by comparing the most analogous image and the image of the terminal fittings, to which the electric wire is pressure-welded, mounted on the insulator picked up by the image pickup means.

With the construction described above, since a plurality of the images of a terminal fittings to be mounted on the insulator and a plurality of the images of a terminal fittings to which the wire is pressure-welded are stored in advance. Out of these images, an image most analogous to the image picked up by the image pickup means is extracted.

Therefore, an image analogous to the image of the terminal fittings picked up by the image pickup means can be included in the image consulting data and the second image consulting data with high possibility. Therefore, the image of the terminal fittings picked up by the image pickup means can very well coincide with the image most analogous to the image thereof out of the stored images in the image consulting data. In addition, the quality of the mounting state of the terminal fittings on the insulator and the quality of the pressure-welding state of the wire are judged by comparing the most analogous image and the image picked up by the image pickup means. Therefore, a mistake in detection such as judging a non-defective part to be a defective part can be prevented.

preferably, the image is a digital information, in which an optical power is indicated with a plurality of grades thereof, the extraction means compares the image of the terminal fittings picked up by the image pickup means and a plurality of the image in the image consulting data by a method of normalization correlation so that the image having the highest correlation value obtained by the method of normalization correlation out of the images is set up to be said most analogous image, the judgment means judges the quality of the mounting state of the terminal fittings on the insulator to be good when the correlation value is equal to or higher than a predetermined threshold while judges the quality of the mounting state to be no good when the correlation value is lower than the predetermined threshold, the second extraction means compares the image of the terminal fittings, to which the electric wire is pressure-welded, picked up by the image pickup means and a plurality of the images in the second image consulting data by a method of normalization correlation so that the image having the highest correlation value obtained by the method of normalization correlation out of the images is set up to be said most analogous image, and the second judgment means judges the quality of the pressure-welding state of the electric wire to the terminal fittings to be good when the correlation value is equal to or higher than a predetermined threshold while judges the quality of the pressure-welding state to be no good when the correlation value is lower than the predetermined threshold.

In the construction described above, the method of normalization correlation is employed. That is, two images to be compared are relatively moved, enlarged and reduced so as to match their size with each other (i.e. to carry out the normalization). After this normalization, the correlation is carried out so as to calculate the correlation value indicating the degree of coincidence between the two images.

Since the normalization correlation method is carried out, the two images, in which an optical power is indicated with a plurality of grades, are matched with each other. The images of the same terminal fittings have about the same variation in the optical intensity with each other. Therefore, the degree of coincidence between the images of the same terminal fittings becomes higher compared to a case, in which images recorded in a binary condition are compared with each other. Consequently, since the image picked up by the image pickup means can very well coincides with the most analogous image, a mistake in detection such as judging a non-defective part to be a defective part can be prevented.

Preferably, the terminal fittings has a pressure-welding part to which the electric wire is pressure-welded and a caulking piece for caulking the electric wire, the image pickup means picks up at least one image out of an image of the pressure-welding part and that of the caulking piece, the image consulting data includes at least one plurality of images out of images of the pressure-welding part and those of the caulking piece, and the extraction means compares at least one image out of an image of the pressure-welding part and that of the caulking piece, which are picked up by the image pickup means, with at least one plurality of images out of images of the pressure-welding part and those of the caulking piece, which are included in the image consulting data.

With the construction described above, the quality of the terminal fittings is judged by using at least one set of images out of images of the pressure-welding part and those of the caulking piece. Therefore, can be securely judged is at least one out of whether or not the wire can be securely pressure-welded to the terminal fittings and whether or not the terminal fittings can securely caulk the wire.

Preferably, the terminal fittings has a pressure-welding part to which the electric wire is pressure-welded and a caulking piece for caulking the electric wire, the image pickup means picks up at least one image out of an image of the pressure-welding part to which the electric wire was pressure-welded and that of the caulking piece which caulked the electric wire, the second image consulting data includes at least one plurality of images out of images of the pressure-welding part to which the electric wire was pressure-welded and those of the caulking piece which caulked the electric wire, and the extraction means compares at least one image out of an image of the pressure-welding part to which the electric wire was pressure-welded and that of the caulking piece which caulked the electric wire, which are picked up by the image pickup means, with at least one plurality of images out of images of the pressure-welding part to which the electric wire was pressure-welded and those of the caulking piece which caulked the electric wire, which are included in the second image consulting data.

With the construction described above, the quality of the pressure-welding state of the wire to the terminal fittings is judged by using at least one set of images out of images of the pressure-welding part and those of the caulking piece. Therefore, can be securely judged is at least one out of whether or not the wire can be securely pressure-welded to the terminal fittings and whether or not the terminal fittings can securely caulk the wire.

BRIEF DESCRIPTION OF THE DRAWINGS

FIG. 2 is a table illustrating an image consulting data stored by an image-processing device of the inspection apparatus shown in FIG. 1;

FIG. 3 is a table illustrating a normal data stored by an image-processing device of the inspection apparatus shown in FIG. 1;

FIG. 5 is a flow chart illustrating a flow of inspection by the inspection apparatus shown in FIG. 1;

FIG. 7 is a flow chart illustrating a flow of inspection by an inspection apparatus according to a second embodiment of the present invention;

FIG. 9 is a table illustrating an image consulting data stored by an image-processing device of the inspection apparatus shown in FIG. 8;

FIG. 10 is a table illustrating one example of comparison data before the pressure-welding of a wire stored by an image-processing device of the inspection apparatus shown in FIG. 8;

FIG. 11 is a table illustrating another example of comparison data before the pressure-welding of a wire stored by an image-processing device of the inspection apparatus shown in FIG. 8;

FIG. 14 is a table illustrating a second image consulting data stored by an image-processing device of the inspection apparatus shown in FIG. 8;

FIG. 15 is a table illustrating one example of comparison data after the pressure-welding of a wire stored by an image-processing device of the inspection apparatus shown in FIG. 8;

FIG. 16 is a table illustrating another example of comparison data after the pressure-welding of a wire stored by an image-processing device of the inspection apparatus shown in FIG. 8;

FIG. 22 is a flow chart illustrating a flow for inspecting the mounting state of the pressure-welding terminal for JB on the pressure-welding plate in the flow chart shown in FIG. 21;

FIG. 23 is a flow chart illustrating a flow for inspecting the pressure-welding state of the wire to the pressure-welding terminal for JB in the flow chart shown in FIG. 21;

DESCRIPTION OF THE PREFERRED EMBODIMENTS

Figure 1:
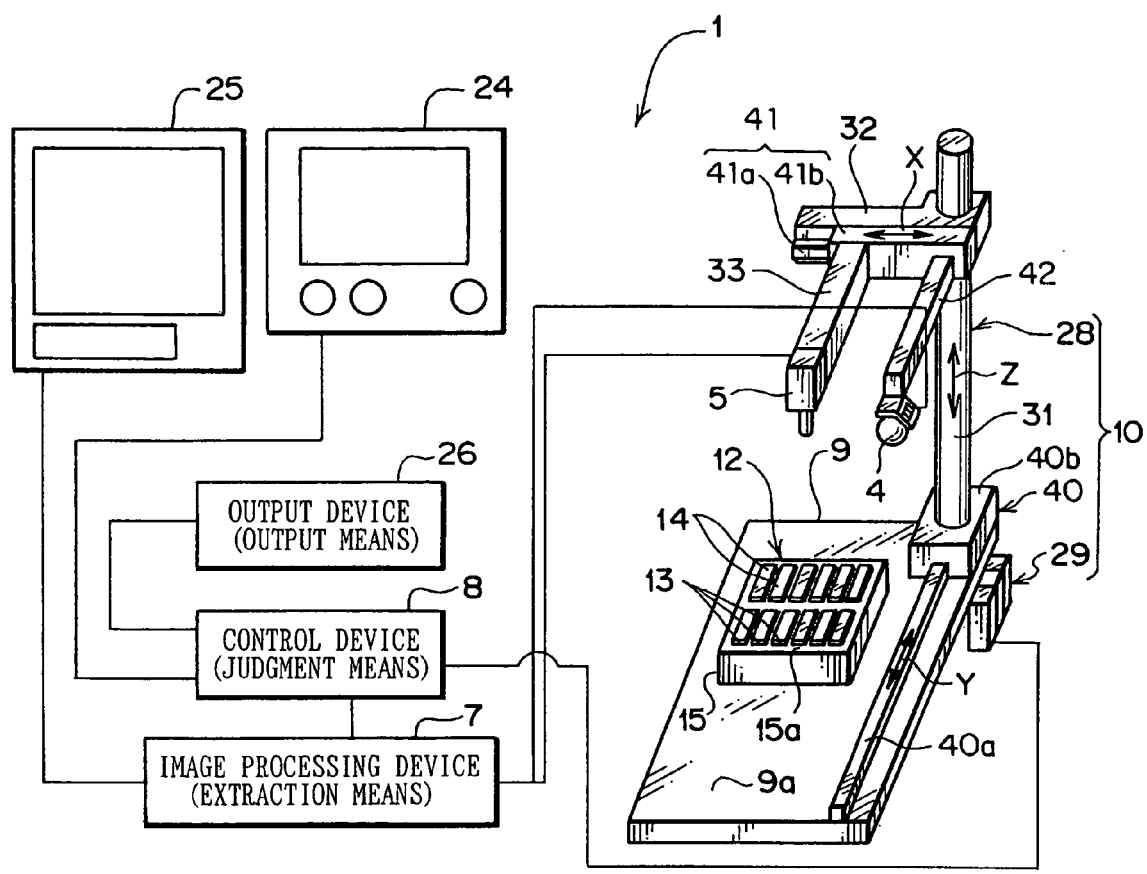
FIG. 1 is a schematic view illustrating a constitution of an inspection apparatus of an electric junction box according to a first embodiment of the present invention.
Figure 6:
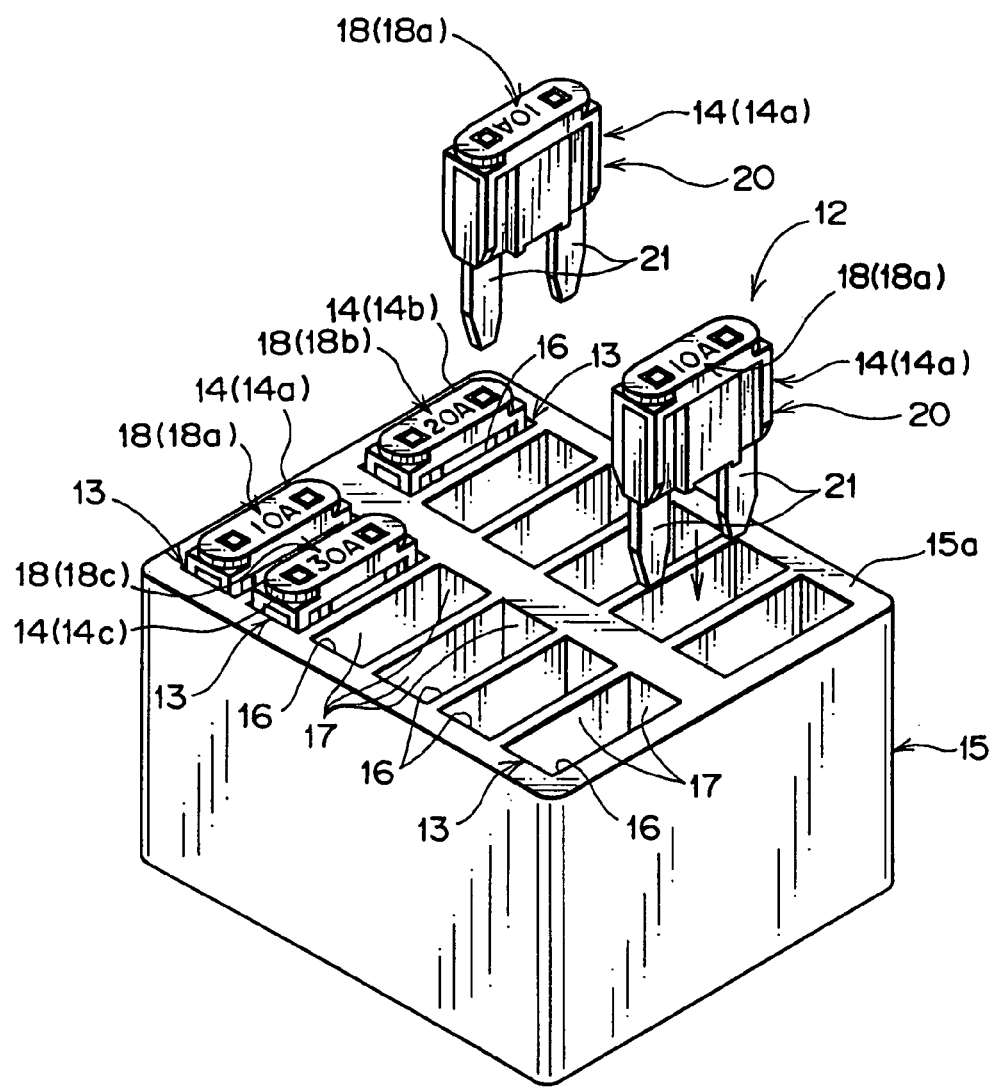
FIG. 6 is a perspective view illustrating an example of an electric junction box as a subject of the inspection by the inspection apparatus shown in FIG. 1.
Figure 8:
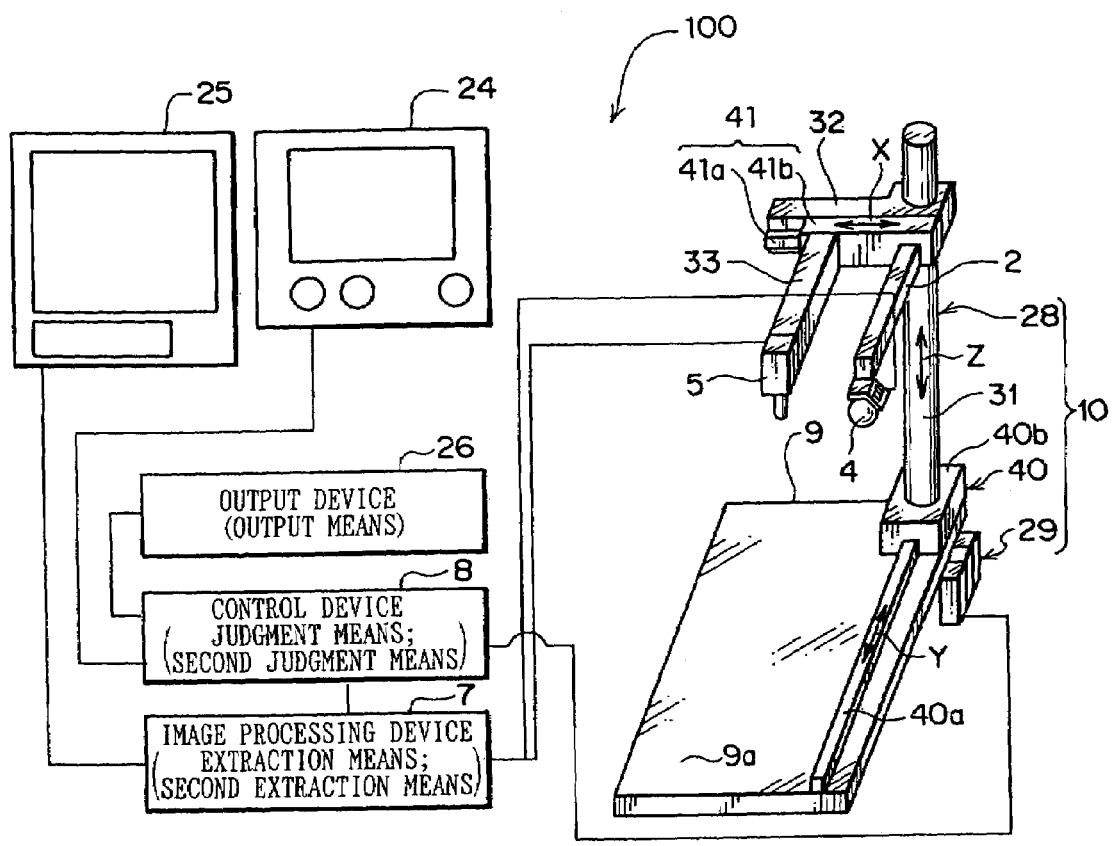
FIG. 8 is a schematic view illustrating a constitution of an inspection apparatus of a terminal fittings according to a third embodiment of the present invention.

In the following, an inspection apparatus of an electric junction box (hereinafter, simply called an inspection apparatus) 1 according to a first preferred embodiment of the present invention will be explained with reference to FIGS. 1–6. The inspection apparatus 1 as shown in FIG. 1 inspects whether or not each fuse 14 as an electric part having a required item symbol is mounted on a corresponding mount 13 in the electric junction box 12 as shown in FIG. 6. The inspection apparatus 1 is used, for example, in a step of testing electric continuity for the electric junction box 12.

In the electric continuity test mentioned above, whether or not the fuse 14 is mounted on the corresponding mount 13 is checked by applying a current to receiving terminals (explained later on) in the electric junction box 12. In this electric continuity test, whether or not an item symbol of the fuse 14 mounted on the mount 13 is proper cannot be judged.

As shown in FIG. 6, the electric junction box 12 includes a box body 15, a plurality of mounts 13 and fuses 14. The mount 13 has an opening 16 opened on a surface 15a out of a plurality of surfaces of the box body 15 and a plurality of walls 17 continued to the periphery of the opening 16. The opening 16 is formed in a rectangular shape in a plan view. The mount 13 receives a pair of the receiving terminals connected to wires and so on.

The fuse 14 has a pair of terminals 21, a housing 20 and a fuse element (not shown in the figure). The terminal 21 is made of electrically conductive metal and formed in a blade-shape. A pair of the terminals 21 is arranged in parallel. The housing 20 is made of insulating synthetic resin and formed in a box-shape. The housing 20 receives each end of a pair of the terminals 21.

The fuse element is received in the housing 20 and connects a pair of the terminals 21 to each other. The fuse element fuses when a current value of the power supplied through a terminal 21 exceeds a predetermined current value.

As for the fuse 14, various current values and permissible current values are set up, at which the fuse element fuses. An item symbol of the fuse 14 is defined depending upon the permissible current value and so on. That is, the fuse 14 has a different permissible current value depending upon the item symbol thereof.

As described in JIS (Japanese Industrial Standard), the permissible current is defined as the maximum current, at which the fuse element shows no deterioration after an electric conduction for a certain period of time under a condition that is prescribed for the fuse element. On an outer surface of the housing 20 of the fuse 14, there is formed a mark 18, which indicates the permissible current value and is made differently depending upon the item symbol of the fuse 14.

In this specification, the fuse 14, the permissible current of which is 10 A (ampere), is hereinafter defined as the fuse 14a having the item symbol A. The fuse 14, the permissible current of which is 20 A (ampere), is hereinafter defined as the fuse 14b having the item symbol B. The fuse 14, the permissible current of which is 30 A (ampere), is hereinafter defined as the fuse 14c having the item symbol C.

On the outer surface of the housing 20 of the fuse 14a, there is formed a mark 18a of "10 A". On the outer surface of the housing 20 of the fuse 14b, there is formed a mark 18b of "20 A". On the outer surface of the housing 20 of the fuse 14c, there is formed a mark 18c of "30 A".

As shown in FIG. 1, the inspection apparatus 1 includes an illumination lamp 4 as an optical source, a CCD camera 5 as the image pickup means, an image-processing device 7 as the extraction means, control device 8 as the judgment means, an inspection table 9, a driving arm unit 10, input device 24, display device 25, and output device 26 as output means.

The lamp 4 provides a light to an electric junction box 12 to be inspected, which is placed on the inspection table 9. The lamp 4 provides a light to the outer surface of the housing 20 of fuses 14a, 14b and 14c in the electric junction box 12. That is, the lamp 4 can provide a light to the marks 18a, 18b and 18c. The lamp 4 is held by a holding arm 42 (explained later on) of the driving arm unit 10. For example, a known halogen lamp having high luminance can be employed as the lamp 4.

The CCD camera 5 can pick up an image of the junction box 12 to be inspected, which is placed on the inspection table 9. The CCD camera 5 can pick up an image of the outer surface of the housing 20 of the fuses 14a, 14b and 14c in the junction box 12. The CCD camera 5 can pick up an image of the marks 18a, 18b and 18c. The CCD camera 5 is held by an Y-axis arm 33 (explained later on) of the driving arm unit 10.

In the figure, the CCD camera 5 has a two-dimensional image sensor, in which the image sensors composing pixels are arranged in two dimensions, and a lens for guiding an image to the two-dimensional image sensor. In the CCD camera 5, the two-dimensional image sensor detects the power of the light with classifying the power into a plurality of grades.

That is, the CCD camera 5 detects the light power at each pixel, which is arranged in two dimensions. The CCD camera 5 picks up so-called black and white images having light and shade. The CCD camera 5 can pick up an image of the marks 18a, 18b and 18c of at least the part of the fuses 14a, 14b and 14c out of the fuses 14a, 14b and 14c in the junction box 12.

The input device 24 is used to input the setting state of the inspection apparatus 1, such as an item symbol and the number of the junction box 12 to be inspected, and the number and the position of the fuses 14a, 14b and 14c, into the control device 8. That is, the input device 24 is used for carrying out the various operations of the inspection apparatus 1. As the input device 24, a known keyboard, mouse, various switches and an operation button can be employed. In the figure, the input device 24 has a plurality of switches and operation buttons.

The display device 25 displays the operating state of the inspection apparatus 1 or the quality of the mounting state of the inspected fuses 14a, 14b and 14c. As the display device 25, a known Cathode Ray Tube (CRT) and a Liquid Crystal Display (LCD) can be used. In the figure, a known CRT is used.

The output device 26 outputs the quality of the mounting state of the inspected fuses 14a, 14b and 14c and so on. As the output device 26, a known printer, which prints out the inspection result, and a CD-ROM driving device, which can write the inspection result into various record media such as a CD-ROM as an electronic information, can be used.

The inspection table 9 has a flat surface 9a extending horizontally, on which the junction box 12 to be inspected can be placed.

The driving arm unit 10 has a driving arm 28 and a driving control section 29. The driving arm 28 can be slide along the surface 9a by a known linear guide 40 and the like with respect to the inspection table 9. In the figure, the arm 28 can slide along arrow Y in the direction from this side to the opposite side or the direction from the opposite side to this side. The linear guide 40 has a rail 40a mounted on the table 9 extending along arrow Y and a slider 40b provided movable with respect to the rail 40a.

The driving arm 28 has a Z-axis arm 31 extending along the vertical direction, an X-axis arm 32 and an Y-axis arm 33. One end of the Z-axis arm 31 is fixed to the slider 40b. The X-axis arm 32 is held movable along the crossing direction with regard to both of the surface 9a and arrow Y in relation to the Z-axis arm 31.

In the figure, the X-axis arm 32 is movable in relation to the Z-axis arm 31 along arrow Z in FIG. 1, which crosses with regard to arrow Y and is along the vertical direction. The X-axis arm 32 is formed in an arm-shape extending along the direction, which is along the surface 9a and crosses with regard to arrow Y. In the figure, the X-axis arm extends along arrow X crossing with regard to both of arrow Y and arrow Z.

The Y-axis arm 33 is held by a known linear guide 41 to be movable along arrow X in relation to the X-axis arm. The linear guide 41 has a rail 41a mounted on the X-axis arm extending along arrow X and a slider 41b provided to be movable in relation to the rail 41a.

One end of the Y-axis arm 33 is fixed to the slider 41b. The Y-axis arm 33 is formed in an arm-shape extending along arrow Y. A CCD camera 5 is mounted on an opposite end of the Y-axis arm 33.

An illumination lamp 4 is mounted on the slider 41b through a holding arm 42. The holding arm 42 is formed in an arm-shape extending along arrow Y and one end thereof is fixed to the slider 41b. An illumination lamp 4 is mounted on an opposite end of the holding arm 42.

The lamp 4 and the CCD camera 5 are arranged at a position where a light from the lamp 4, which reflects on an outer surface of the housing 20 of the junction box 12 to be inspected, launches.

The driving arm 28 is moved along arrow Y by a known air cylinder or a motor. The X-axis arm 32 is moved along arrow Z by a known air cylinder or a motor. The Y-axis arm 33 is moved along arrow X by a known air cylinder or a motor.

The driving control section 29 drives an air cylinder or a motor, which is for moving the driving arm 30, the X-axis arm 32 and the Y-axis arm 33, in response to a command from the control device 8. With the construction mentioned above, the driving arm unit 10 moves the illumination lamp 4 and the CCD camera 5 along arrows Y, Z and X shown in FIG. 1. The driving arm unit 10 situates the CCD camera 5 at a position where the CCD camera 5 can pick up images of all of the fuses 14a, 14b and 14c in the junction box 12 in response to a command from the control device 8.

The image-processing device 7 is a computer that includes a known Central Processing Unit (CPU), a Read-only memory (ROM) and a Random Access Memory (RAM). The image-processing device 7 is connected to the illumination lamp 4, the CCD camera 5, the display device 25 and the control device 8.

Figure 4:
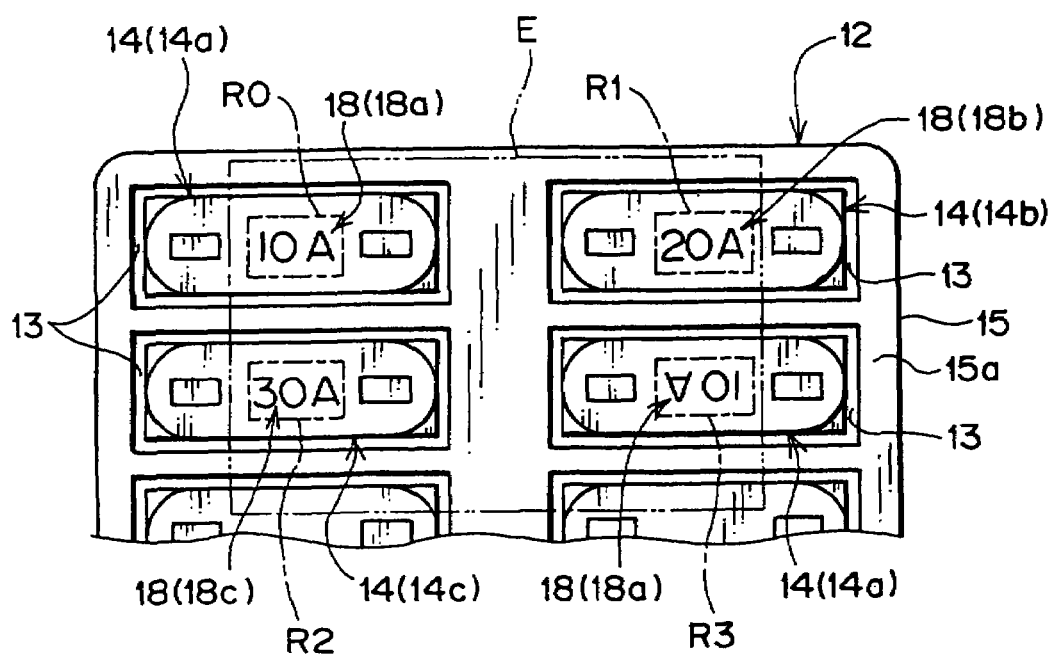
FIG. 4 is a view illustrating an example of an image picked up by a CCD camera of the inspection apparatus shown in FIG. 1.

The image-processing device 7 takes in each image E (a section surrounded by an alternate long and two short dashes line shown in FIG. 4) of the fuses 14a, 14b and 14c, which is picked up by the CCD camera 5, and stores the same. This image is a digital image, in which an optical power is indicated with 256 grades, in each pixel arranged in two dimensions.

The image-processing device 7 stores positions of sections R0, R1, R2, R3, - - - , and RN (a section surrounded by an alternate long and short dash line shown in FIG. 4) to be inspected in the digital image from the CCD camera 5. Here, each of the sections R0, R1, R2, R3, - - -, and RN to be inspected is a section, which is provided corresponding to each fuse 14a, 14b or 14c out of the images of the fuses 14a, 14b and 14c mounted on the corresponding mount 13 in the junction box 12, and includes the marks 18a, 18b and 18c of the fuses 14a, 14b and 14c, respectively.

The image-processing device 7 stores an image consulting data 2 shown in FIG. 2. The image consulting data 2 stores a plurality of images for each marks 18a, 18b and 18c with respect to the corresponding fuses 14a, 14b and 14c with whole item symbols, which are used in the junction box 12. That is, the image consulting data 2 stores images including marks 18 of the fuses 14 of whole item symbols used in the junction box 12. A plurality of images including the mark 18 for the fuse 14 having one item symbol are stored. Among these images, there are different images having different effects of light or different situations of the mark 18a, 18b or 18c.

The image-processing device 7 compares each image of the sections R0, R1, R2, R3, - - -, and RN to be inspected with all the images stored in the image consulting data 2. That is, the image-processing device 7 compares images including the mark 18 of the fuse 14, which is mounted on the corresponding mount, picked up by the CCD camera 5 with all the images stored in the image consulting data 2.

When the image-processing device 7 compares each image of the section R0, R1, R2, R3, - - -, and RN to be inspected with the corresponding images stored in the image consulting data 2, the device 7 first carries out a normalization processing. In the normalization process, two images subjected to the comparison are relatively moved, enlarged and reduced so as to adjust their size (that is, to normalize). Thereafter, on the basis of a known correlation method, a correlation value indicating the degree of coincidence between the two images is computed. Thus, the image-processing device 7 compares each image of the section R0, R1, R2, R3, - - -, and RN to be inspected with the corresponding images stored in the image consulting data 2 by using a method of normalization correlation.

The image-processing device 7 extracts an image having the maximum correlation value from the images stored in the image consulting data with respect to every section R0, R1, R2, R3, - - -, and RN to be inspected. The image-processing device 7 determines an item symbol of the fuse 14, which corresponds to the image having the maximum correlation value. The image-processing device 7 set up the image having the maximum correlation value to be the most analogous image.

Thus, the image-processing device 7 extracts an item symbol of the fuse 14 having an image most analogous to each image of the sections R0, R1, R2, R3, - - -, and RN to be inspected from the images stored in the image consulting data. The image-processing device 7 outputs, the item symbol of the fuse 14 having the most analogous image extracted with respect to every section R0, R1, R2, R3, - - -, and RN to be inspected, to the control device 8. In addition, the image-processing device 7 outputs images during the comparison to the display device 25, which displays the image.

The control device 8 is a computer having a known CPU, ROM and RAM. The control device 8 is connected to the drive control section 29, input device 24, output device 26 and the image-processing device 7. The control device 8 controls the drive control section 29, input device 24, output device 26 and the image-processing device 7 so as to control whole of the inspection apparatus 1.

The control device 8 controls the drive control section 29 so as to drive each cylinder or motor of the driving arm unit 10, thereby making the CCD camera 5 successively pick up an image of the junction box 12. In this connection, if the CCD camera cannot pick up images of the marks 18a, 18b and 18c of all the corresponding fuses 14a, 14b and 14c at one time, the CCD camera separately picks up the images in a plurality of times. Thus, when the control device 8 makes the CCD camera separately pick up the images in a plurality of times, the control device 8 suitably drives each cylinder or motor of the driving arm unit 10.

The control device 8 stores a normal data 3 shown in FIG. 3. The normal data indicates an item symbol of the fuse 14 located each section R0, R1, R2, R3, - - -, and RN to be inspected when all the fuses 14a, 14b and 14c are properly mounted on their corresponding mounts 13. That is, the normal data indicates an item symbol of the fuse 14, which is properly mounted on the corresponding mount 13.

The control device 8 compares an item symbol of the fuse 14 most analogous to an image of each section R0, R1, R2, R3, - - -, and RN to be inspected, which is input from the image-processing device 7, with the normal data. The control device 8 judges that a proper fuse 14 is mounted on the corresponding mount 13 when the item symbol of the most analogous fuse 14 coincides with the normal data. On the other hand, the control device 8 judges that an improper fuse 14 is mounted on the corresponding mount 13 when the item symbol of the most analogous fuse 14 does not coincide with the normal data.

The control device 8 outputs the following information to the output device 26: that the junction box 12 is good, in which the proper fuses 14 are mounted on all of the corresponding mounts 13; that the junction box 12 is no good; and when the junction box 12 is no good, the mount 13 on which the fuse 14 having the improper item symbol, that is, the section R0, R1, R2, R3, - - -, and RN to be inspected, which includes such a mount 13 on which the fuse 14 having the improper item symbol.

As for the inspection apparatus 1 according to this preferred embodiment, when an electric junction box 12 is inspected, first in step S1 as shown in FIG. 5, the control device 8 controls the drive control section 29 so as to make the CCD camera 5 face a fuse 14 and to make the CCD camera pick up an image of the fuse 14 in the junction box 12, thereby outputting the image to the image-processing device 7. The image-processing device 7 stores the image sent from the CCD camera and the system advances to step S2.

At the step S1, the image, which is picked up by the CCD camera 5 and stored in the control device 8, is a digital image of two dimensions, in which an optical power is indicated with 256 grades.

In step S2, the image-processing device 7 extracts images of sections R0, R1, R2, R3, - - -, and RN to be inspected from the images picked up by the CCD camera 5. The image-processing device 7 compares each image of sections R0, R1, R2, R3, - - -, and RN to be inspected with all of the images stored in the image consulting data 2, then advancing to step S3.

In step S3, the image-processing device 7 extracts an image most analogous to each image of sections R0, R1, R2, R3, - - -, and RN to be inspected from the image consulting data 2. The image-processing device 7 extracts an item symbol of the fuse 14 having an image most analogous to each image of sections R0, R1, R2, R3, - - -, and RN to be inspected. Then, the image-processing device 7 outputs the item symbol of the fuse 14 having the most analogous image to the control device 8, then advancing to step S4.

In step S4, it is judged whether or not the image-processing device 7 extracts an item symbol of the fuse 14 having the most analogous image with regard to all of the images of sections R0, R1, R2, R3, - - -, and RN to be inspected. If judged YES, the system advances to step S5. On the other hand, if judged NO, that is, if there is a section R0, R1, R2, R3, - - -, or RN to be inspected, in which the item symbol of the fuse 14 having the most analogous image is not extracted, the system comes back to the step S2 and starts again from the step S2.

In step S5, the control device 8 compares an item symbol of the fuse 14 having an image most analogous to the image of section R0, R1, R2, R3, - - -, and RN to be inspected with the normal data 3. When all of the item symbols of the fuse 14 having an image most analogous to the image of section R0, R1, R2, R3, - - -, and RN to be inspected coincides with the normal data 3, the control device 8 judges the mounting state of the fuse 14 in the junction box 12 to be good, that is, judges the junction box 12 to be non-defective.

On the other hand, when at least one of the item symbols of the fuse 14 having an image most analogous to the image of section R0, R1, R2, R3, - - -, and RN to be inspected does not coincide with the normal data 3, the control device 8 outputs the mount on which the fuse 14 having the improper item symbol is mounted, that is, a section including such a mount, to the output device 26.

In addition, when at least one of the item symbols of the fuse 14 having an image most analogous to the image of section R0, R1, R2, R3, - - -, and RN to be inspected does not coincide with the normal data 3, the control device 8 judges the mounting state of the fuse 14 in the junction box 12 to be no good, that is, judges the junction box 12 to be defective, then advancing to step S6.

In step S6, the result of the judgement by the control device 8 is output by the output device 26 with printing and stored in the storing medium described above.

According to the preferred embodiment, the image-processing device 7 stores plurality of images of fuses 14_a_, 14_b_ and 14_c_, which are mounted in the junction box 12, in the image consulting data in advance. The image-processing device 7 extracts an image most analogous to the image picked up by the CCD camera 5 from the image consulting data 2.

Thus, since a plurality of images are stored with regard to one item symbol, the degree of coincidence between the image picked up by the CCD camera 5 and the most analogous image is high. Therefore, each item symbol of the fuses 14_a_, 14_b_ and 14_c_, which is mounted on the mount 13, can be easily distinguished, that is, an error of mounting of the fuse 14 can be easily detected.

The control device 8 judges whether or not the proper fuses 14 are mounted on the corresponding mounts 13 by comparing the item symbols of the fuses 14 having the most analogous image with the normal data. Therefore, when the item symbol of the fuse 14 having the most analogous image, which is extracted by the image-processing device 7, is in error, that the fuse 14 having a wrong item symbol is mounted on the mount can be securely detected. Thus, a right judgement is always done.

In addition, when comparing the images picked up by the CCD camera 5 with the images in the image consulting data, the normalization correlation method is used. The matching (comparison) is carried out for images, in which the power of the light changes step by step, with each other. Therefore, the degree of coincidence between the images having the same item symbol is high.

Consequently, the degree of coincidence between the images picked up by the CCD camera 5 and the most analogous image in the image consulting data is high, thereby the item symbol of the fuse 14 mounted on the mount 13 can be more securely distinguished. Therefore, an error of mounting of the fuse 14 can be more securely detected.

In the following, an inspection apparatus 1 according to a second preferred embodiment of the present invention will be explained with reference to FIG. 7. The same numbering of the steps are used for each substantially same step.

The inspection apparatus 1 according to the second preferred embodiment has the same structure as that according to the first preferred embodiment shown in FIG. 1 and so on. An image-processing device 7 of the inspection apparatus 1 according to this embodiment also stores a normal data 3 and an image consulting data 2.

The image-processing device 7 takes in the image E of the junction box 12 picked up by the CCD camera 5 and preserves the image. The image-processing device 7 extracts an item symbol of the fuse 14, which is properly mounted on the corresponding mount, on the basis of the normal data 3. The image-processing device 7 compares each image of the sections R0, R1, R2, R3, - - -, and RN to be inspected with all of the images of the fuses 14 having a proper item symbol, which are stored in the image consulting data 2.

When comparing the images with each other, the image-processing device 7 uses a method of normalization correlation, similarly to the first preferred embodiment. The image-processing device 7 computes each correlation value for the images of the sections to be inspected with respect to every image of the fuses 14 having the proper item symbol.

The image-processing device 7 extracts an image having the maximum correlation value in relation to the images of the sections to be inspected, then outputs the maximum correlation value to the control device 8.

The control device 8 judges whether or not the maximum correlation value described above is equal to or more than a predetermined value, which is suitably determined according to the item symbol of the fuse 14.

When the correlation value is equal to or more than the predetermined value, the control device 8 judges that the fuse 14 having the proper item symbol is mounted on the mount 13. On the other hand, when the correlation value is less than the predetermined value, the control device 8 judges that the fuse 14 having the improper item symbol is mounted on the mount 13.

When all of the mounts 13 mount the fuses 14 having the proper item symbol, the control device 8 judges the junction box 12 to be non-defective. On the other hand, when at least one of the mounts 13 mounts the fuses 14 having the improper item symbol, the control device 8 judges the junction box 12 to be defective. The control device 8 outputs the result of judging whether or not the junction box 12 is non-defective to the output device 26. When judged defective, the control device 8 outputs the mount 13, on which the fuse 14 having the improper item symbol is mounted, to the output device 26.

The inspection apparatus 1 according to the preferred embodiment judges the quality of the mounting state of the fuses 14 in accordance with a flow chart shown in FIG. 7. Similarly to the first embodiment described above, in step S1, the CCD camera 5 picks up the image E and the image-processing device 7 stores the images from the CCD camera 5, then advancing to step S2a.

In step S2a, on the basis of the normal data 3, the image-processing device 7 extracts the item symbol of the fuse 14 to be mounted on each mount 13, that is, the item symbol of the fuse 14, which is properly mounted on the corresponding mount, shown in each sections R0, R1, R2, R3, - - - , and RN to be inspected.

Then, by using the normalization correlation method, the image-processing device 7 compares each image of the sections to be inspected with all of the images of the fuse 14 having the proper item symbol, which are stored in the image consulting data 2. The image-processing device 7 extracts the maximum correlation value from the correlation values of the images in the image consulting data 2, then advancing to step S4.

In step S4, it is judged whether or not the image-processing device 7 extracts the maximum correlation value with regard to all of the images of sections R0, R1, R2, R3, - - - , and RN to be inspected. If judged YES, the system advances to step S5. On the other hand, if judged NO, that is, if there is a section R0, R1, R2, R3, - - - , or RN to be inspected, in which the maximum correlation value is not extracted, the system comes back to the step S2 and starts again from the step S2.

In step S5a, the control device 8 compares the maximum correlation value extracted for every section to be inspected with the predetermined value. When all of the maximum correlation values are equal to or more than the predetermined value, the control device 8 judges the mounting state of the fuse 14 to be good, that is, the junction box 12 to be non-defective.

On the other hand, when at least one of the maximum correlation values is less than the predetermined value, the control device 8 outputs the mount 13, on which the fuse 14 having the improper item symbol is mounted, that is, the section to be inspected, which includes such a mount 13, to the output device 26, and judges the mounting state of the fuses 14 to be no good, that is, judges the junction box to be defective, then advancing to step S6.

In step S6, the result of the judgement by the control device 8 is output by the output device 26 with printing and stored in the storing medium described above.

According to the preferred embodiment, the images picked up by the CCD camera 5 are compared with a plurality of images of the fuse 14 having the proper item symbol, which is mounted on the mount 13, by using the method of normalization correlation. On the basis of the correlation value obtained by the normalization correlation, it is judged whether or not the fuses 14 having the proper item symbol is mounted on the corresponding mount 13.

A plurality of images for each fuse 14a, 14b and 14c to be mounted in the junction box 12 are stored in the image consulting data 2. Therefore, an image analogous to the image of the fuse 14 picked up by the CCD camera 5 is included in the image consulting data 2 with high probability.

Consequently, the degree of coincidence between the image picked up by the CCD camera 5 and the most analogous image out of the images stored in the image consulting data 2 is high. Therefore, it can be securely judged whether or not the fuse 14 is properly mounted on the corresponding mount 13, that is, an error of mounting of the fuse 14 can be detected.

In addition, since the normalization correlation method is used when the image-processing device 7 compares the images with each other, the degree of coincidence between the images of the fuses 14 having the same item symbol is high. Therefore, the item symbol of the fuses 14 mounted on the mount 13 can be more securely distinguished, that is, an error of the mounting of the fuses 14 can be more securely detected.

In addition, since the image-processing device 7 uses only the images of the fuse 14, which is properly mounted on the corresponding mount 13, when comparing the images with each other, a period of time elapsed for the comparison can be shortened. Therefore, a period of time required for the inspection of the junction box can be reduced.

As for the inspection apparatus 1 according to the first and second preferred embodiments, if there is indeed a properly mounted fuse 14 out of the fuses 14, which are judged to be improperly mounted on the mount 13, preferably the control device 8 adds the image of such a properly mounted fuse 14 including the mark 18 to the images in the image consulting data 2.

With the construction described above, an image analogous to the image of the fuse 14, which is picked up by the CCD camera 5, can be included in the images stored in the image consulting data 2 with high probability. Therefore, the degree of coincidence between the image picked up by the CCD camera 5 and the most analogous image extracted from the image consulting data 2 becomes high. Therefore, the item symbol of the fuse 14, which is mounted on the mount 13, can be more securely distinguished, that is, an error of the mounting of the fuse 14 can be more securely detected.

In addition, the inspection apparatus 1 according to the first and second preferred embodiment judge the quality of the mounting state of the fuses 14 mounted in the junction box 12. In the present invention, by using an item symbol of an electric part such as a relay, diode and fusible link, instead of the item symbol of the fuse 14, the quality of the mounting state of a relay, diode or fusible link can be judged.

By using the inspection apparatus 1 according to the first and second preferred embodiments, the following inspection methods for inspecting an electric part can be obtained. One of them is an inspection method of a fuse 14 as an electric part comprising the steps of:

storing a plurality of images of a fuse 14 as a non-defective electric part in advance; and judging whether or not a fuse 14 having a proper item symbol is mounted on the mount 13 on the basis of an image of the fuse 14 to be inspected and a plurality of the images of the non-defective fuse 14, that is, judging whether or not the fuse 14 to be inspected is non-defective.

Another of them is an inspection method of a fuse 14 as an electric part comprising the steps of:

storing a plurality of images of a fuse 14 as a non-defective electric part in advance;

comparing an image of a fuse 14 to be inspected and a plurality of the images of a non-defective fuse 14;

extracting an image most analogous to the image of the fuse 14 to be inspected from a plurality of the images of a non-defective fuse 14; and judging whether or not a fuse 14 having a proper item symbol is mounted on the mount 13 on the basis of the most analogous image and the image of the fuse 14 to be inspected, that is, judging whether or not the fuse 14 to be inspected is non-defective.

With the inspection methods described above, a plurality of images of non-defective fuse 14 are stored in advance. Thereby, an image analogous to the image of the fuse 14 to be inspected can be included in a plurality of the stored images of non-defective fuse 14 with high probability.

Therefore, the degree of coincidence between the image of the fuse 14 to be inspected and an image most analogous to the image of the fuse 14 to be inspected out of a plurality of the stored images of non-defective fuse 14 becomes high. Consequently, an error of judging the quality of the fuse 14 can be prevented from occurring, that is, the quality of the fuse 14 can be securely judged.

In the following, an inspection apparatus for inspecting a terminal fittings according to a third preferred embodiment of the present invention will be explained with reference to FIGS. 8–23. The same reference numeral is used for each substantially same component as that of the inspection apparatus 1 of the junction box, which is described in the first and second preferred embodiments.

Figure 19:
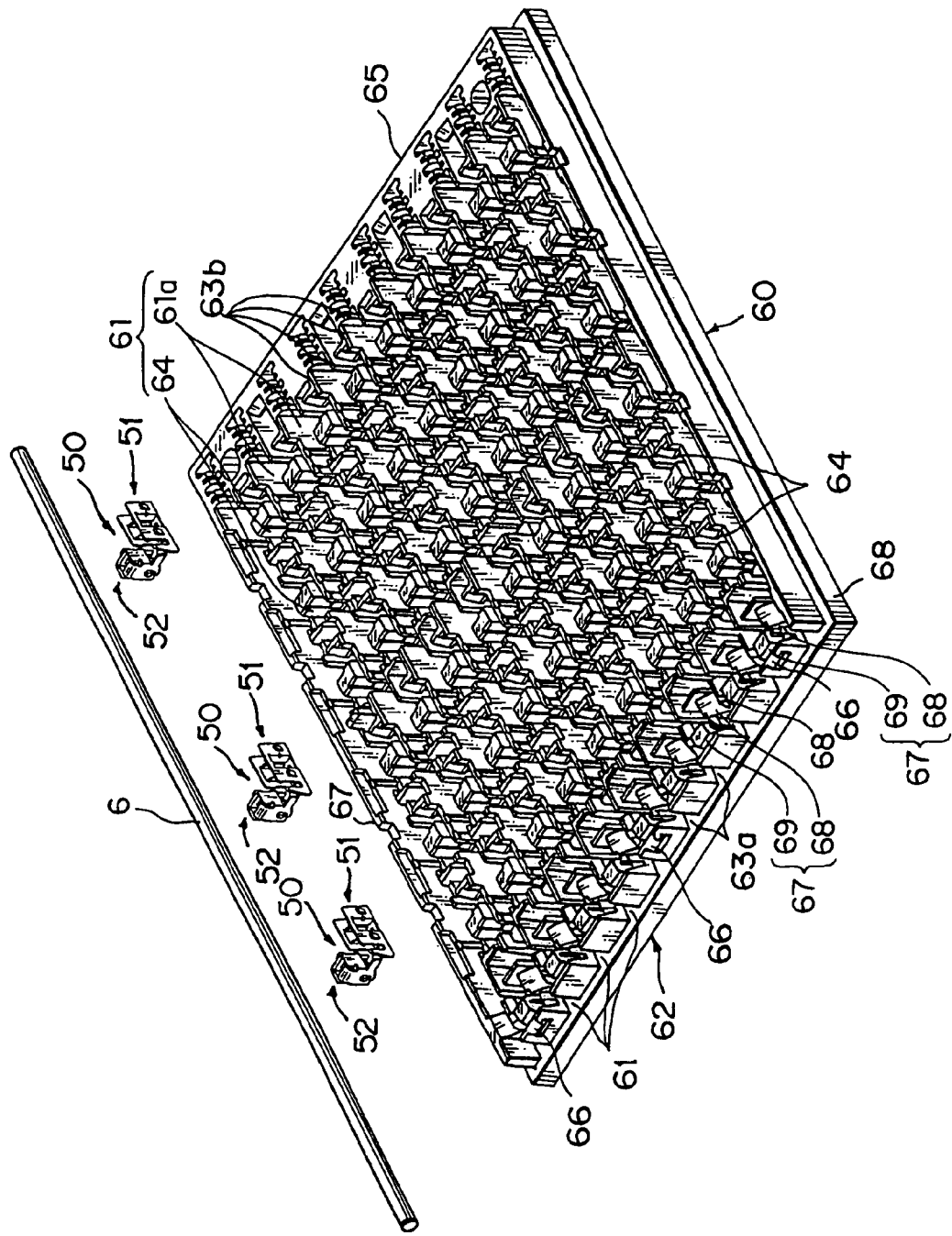
FIG. 19 is a perspective view illustrating a pressure-welding plate, on which a pressure-welding terminal for JB to be inspected by the inspection apparatus shown in FIG. 8 is mounted.

An inspection device 100 described in this preferred embodiment inspects the quality of the mounting state of a pressure-welding terminal 50 for JB (junction box) as a terminal fittings mounted on a pressure-welding plate 60 as an insulator, which is shown in FIG. 19. In addition, the inspection device 100 inspects the quality of the pressure-welding state (fixing state) of an electric wire 6 to the pressure-welding terminal 50 for JB mounted on the pressure-welding plate 60. Here, the pressure-welding terminal 50 for JB as a terminal fittings is an electric part described in the present specification.

Figure 20:
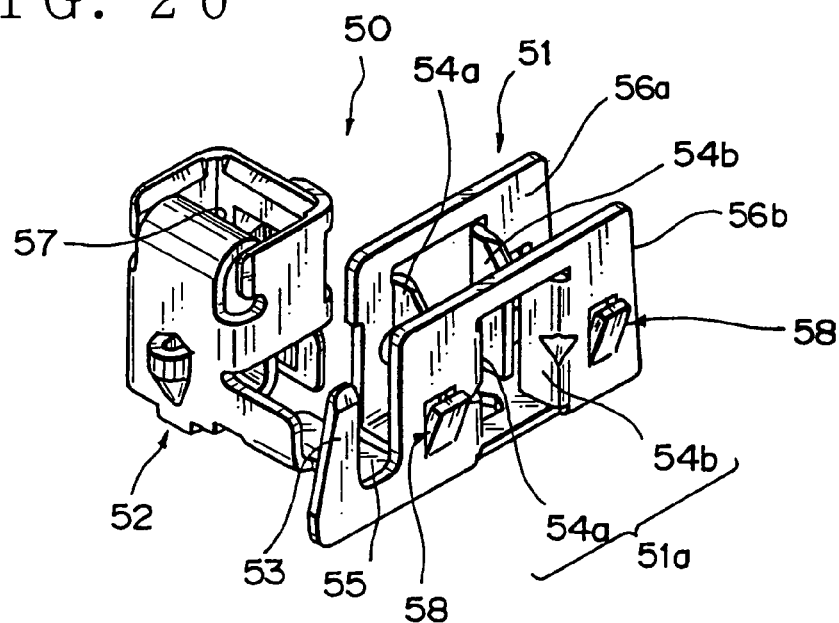
FIG. 20 is a perspective view of a pressure-welding terminal for JB to be inspected by the inspection apparatus shown in FIG. 8.

The pressure-welding terminal 50 for JB is obtained by bending an electrically conductive sheet metal. As shown in FIG. 20, the pressure-welding terminal 50 for JB has a wire connecting part 51, an electric contact 52, and a plurality of locking pieces 58. The wire connecting part 51 has a flat wall 55 on which the wire 6 is placed, a pair of side walls 56a and 56b, a caulking piece 53, and a pressure-welding part 51a.

The wall 55 is formed in a band plate-shape. A pair of the side walls 56a and 56b also are formed in a band plate-shaped. A pair of the side walls 56a and 56b continue to both peripheries of the wall 55 in the width direction thereof arising perpendicularly from the wall 55. A pair of the side walls 56a and 56b positions the wire 6, which is pressure-welded to the pressure-welding part 51a, between the side walls 56a and 56b.

The caulking piece 53 continues to both peripheries of the wall 55 in the width direction thereof arising perpendicularly from the wall 55. The caulking piece 53 puts the wire 6 between the caulking piece 53 and the wall 55 by being bent so as to hang over the wall 55 and holds the wire 6. That is, the caulking piece 53 caulks the wire 6 on the wall 55.

The pressure-welding part 51a has two pairs of pressure-welding blades 54a and 54b facing to each other. The blades 54a and 54b arise perpendicularly from the wall 55. A pair of the blades 54a protrudes in the direction, in which a pair of side walls 56a and 56b approaches to each other, from the inner surface of the side walls 56a and 56b. A pair of the pressure-welding blades 54a cuts into a coated part of the wire 6 so as to come in contact with the core of the wire 6 by the wire 6 being press-fit between a pair of the blades 54a. A pair of the blades 54b also protrudes in the direction, in which a pair of side walls 56a and 56b approaches to each other, from the inner surface of the side walls 56a and 56b. A pair of the pressure-welding blades 54b cuts into a coated part of the wire 6 so as to come in contact with the core of the wire 6 by the wire 6 being press-fit between a pair of the blades 54b. The pressure-welding blades 54a and 54b electrically connects with the wire 6, that is, pressure-weld to the wire 6.

The electric contact 52 continues to one of the periphery of the wall 55 in the length direction thereof. The electric contact 52 and the wire connecting part 51 are arranged at a position where the plan shape of the pressure-welding terminal 50 for JB is L-shaped. The electric contact 52 is formed in a square cylinder-shape. The electric contact 52 is arranged in a manner that the cylinder hole of the electric contact 52 communicates with a hole (not shown in the figure) of the pressure-welding plate 60. A connection bar (not shown in the figure) as connecting means is inserted into the cylinder hole of the electric contact 52.

The connection bar is made of conductive metal and formed in a band plate-shape. The electric contact 52 is provided with a connecting spring piece 57 in the cylinder hole thereof. The connecting spring piece 57 presses the connection bar toward the inner surface of the cylinder hole and electrically connects the connection bar with the electric contact 52.

When the pressure-welding plates 60 are laminated to each other, the connection bar is inserted into the cylinder hole so that the electric contact 52 electrically connects the pressure-welding terminals 50 for JB, which are laminated to each other, with each other. Thus, the electric contact 52 connects with another pressure-welding terminal for JB as another terminal fittings.

The locking piece 58 is formed by notching each part of the side walls 56a and 56b. Each side wall 56a and 56b is provided with the locking piece 58. One end of the locking piece 58 continues to the side walls 56a and 56b and another end thereof is apart from the side walls 56a and 56b. Said another end of the locking piece 58 protrudes toward the outside from the outer surface of the side walls 56a and 56b. When the pressure-welding terminal 50 for JB is mounted on the pressure-welding plate 60, said another end of the locking piece 58 can engage with the inner surface of a partition wall 63b (explained later on).

As for the pressure-welding terminal 50 for JB, the wire connecting part 51 is received into a groove body 61a of a wire-receiving groove 61 (explained later on) of the pressure-welding plate 60, and the electric contact 52 is received into a receiving space 64 (explained later on) of the wire-receiving groove 61. The locking piece 58 is pressed in the direction, in which the space between said other ends shortens, so that the pressure-welding terminal 50 for JB is press-fit into the groove body 61a and the receiving space 64, thereby the pressure-welding terminal 50 for JB is received (or held, or mounted) into the pressure-welding plate 60.

The pressure-welding plate 60 is made of electrically insulating resin and formed in a plate-shape, that is, a flat plate-shape. As shown in FIG. 19, the pressure-welding plate 60 has a rectangular plate body 62, a plurality of wire receiving grooves 61, and a wire fixing part 67. The plate body 62 has a flat base wall 63a, an inner wall 65, and a plurality of partition walls 63b arising perpendicularly from the base wall 63a. The inner wall 65 continues to one periphery located at an inner side of the base wall in FIG. 19. The inner wall 65 arises perpendicularly from the base wall 63a. The partition walls 63b are arranged in parallel with each other leaving a space therebetween. The partition wall 63b crosses at right angle with the inner wall 65 and extends along the length direction of the plate body 62.

The wire-receiving groove 61 is formed being surrounded by the adjacent partition wall 63b and the base wall 63a. The wire receiving grooves 61 are formed in parallel with each other along the width direction of the plate body 62, that is, alone the direction, in which the partition walls 63b are arranged in parallel with each other. The wire-receiving groove 61 extends along the length direction of the plate body 62 and can receive the wire 60 and the pressure-welding terminal 50 for JB.

As shown in FIG. 19, the wire-receiving groove 61 has the groove body 61a and the receiving space 64. The groove body 61a is formed with inner surfaces of the adjacent partition walls 63b and a surface of the base wall 63a. The groove body 61a extends along the partition wall 63b. The groove body 61a receives the wire 60 and the wire connecting part 51 of the pressure-welding terminal 50 for JB.

The receiving space 64 is formed being recessed from the partition wall 63b so as to enlarge the space between a pair of the adjacent partition walls 63b. The receiving space 64 is formed at each of a pair of the adjacent partition walls 63b, which forms one wire-receiving groove 61. The receiving spaces 64 are formed alternately on one partition wall 63b and on another along the length direction of the groove body 61a.

The receiving space 64 receives the electric contact 52 of the pressure-welding terminal 50 for JB and has one hole, which penetrates through the base wall 63a of the plate body 62. Thus, the wire-receiving groove 61 can mount a plurality of the pressure-welding terminals 50 for JB. The receiving space 64 corresponds to the mount, which is described in this specification.

The wire fixing part 67 is provided at the end of the plate body 62, which is apart from the inner wall 65. The wire fixing part 67 has a locking claw 68 and an engaging member 69. A pair of the locking claws 68 is provided corresponding to each wire-receiving groove 61 and arises perpendicularly from both peripheries of the wire-receiving groove 61 in the width direction thereof, that is, arises perpendicularly from the base wall 63a. The locking claw 68 locks up the wire 60 received in the wire-receiving groove 61 and prevents the wire 60 from coming out from the wire-receiving groove 61.

The engaging member 69 is formed between the wire receiving grooves 61 adjoining to each other along the width direction of the wire-receiving groove 61. The engaging member 69 is formed between the locking claws 68 arranged in the wire receiving grooves 61 adjoining to each other and can be engaged between the locking claws 68 adjoining to each other. When the wire 6 is received in the wire-receiving groove 61 and the engaging member 69 engages between the locking claws 68, thereby the wire fixing part 67 prevents the wire 6 from coming out from a pair of the locking claws 68.

The pressure-welding plate 60 has a plurality of locking projections 66 and a plurality of lock receiving projections (not shown in the figure), which engage with each other so as to laminate the pressure-welding plates 60 and to fix them.

The pressure-welding plate 60 arranges the pressure-welding terminals 50 on the base wall 63a along two directions crossing at right angles with each other, the two directions being the length direction of the groove body 61a of the wire-receiving groove 61 and the direction, in which the wire receiving grooves 61 are arranged in parallel with each other. That is, the pressure-welding plate 60 arranges the pressure-welding terminals 50 for JB on the base wall 63a in a two dimensional matrix-shape.

Figure 12:
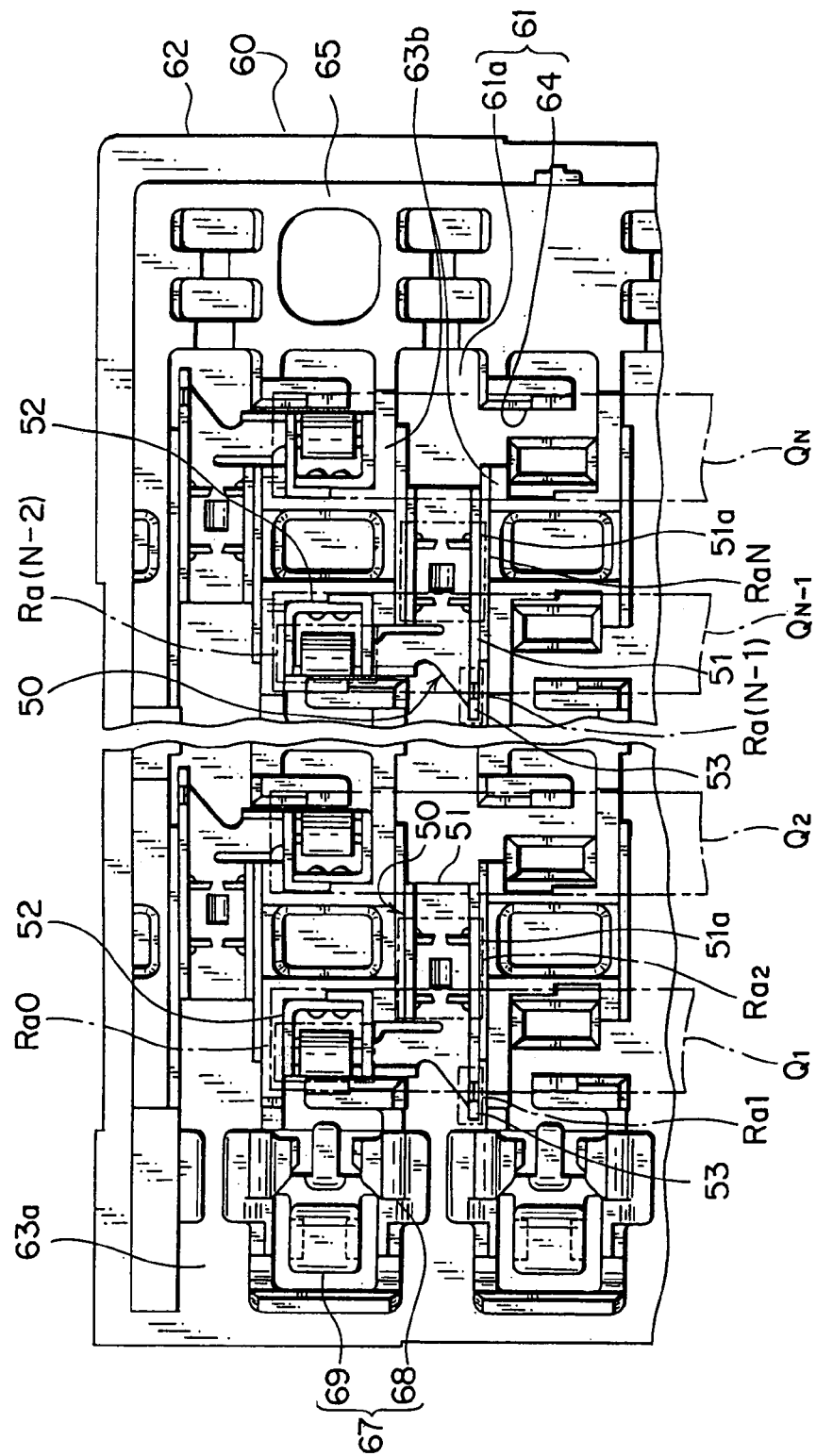
FIG. 12 illustrates one example of an image of a pressure-welding terminal for a junction box (hereinafter, a pressure-welding terminal for JB) before the pressure-welding of a wire picked up by a CCD camera of the inspection apparatus shown in FIG. 8.
Figure 13:
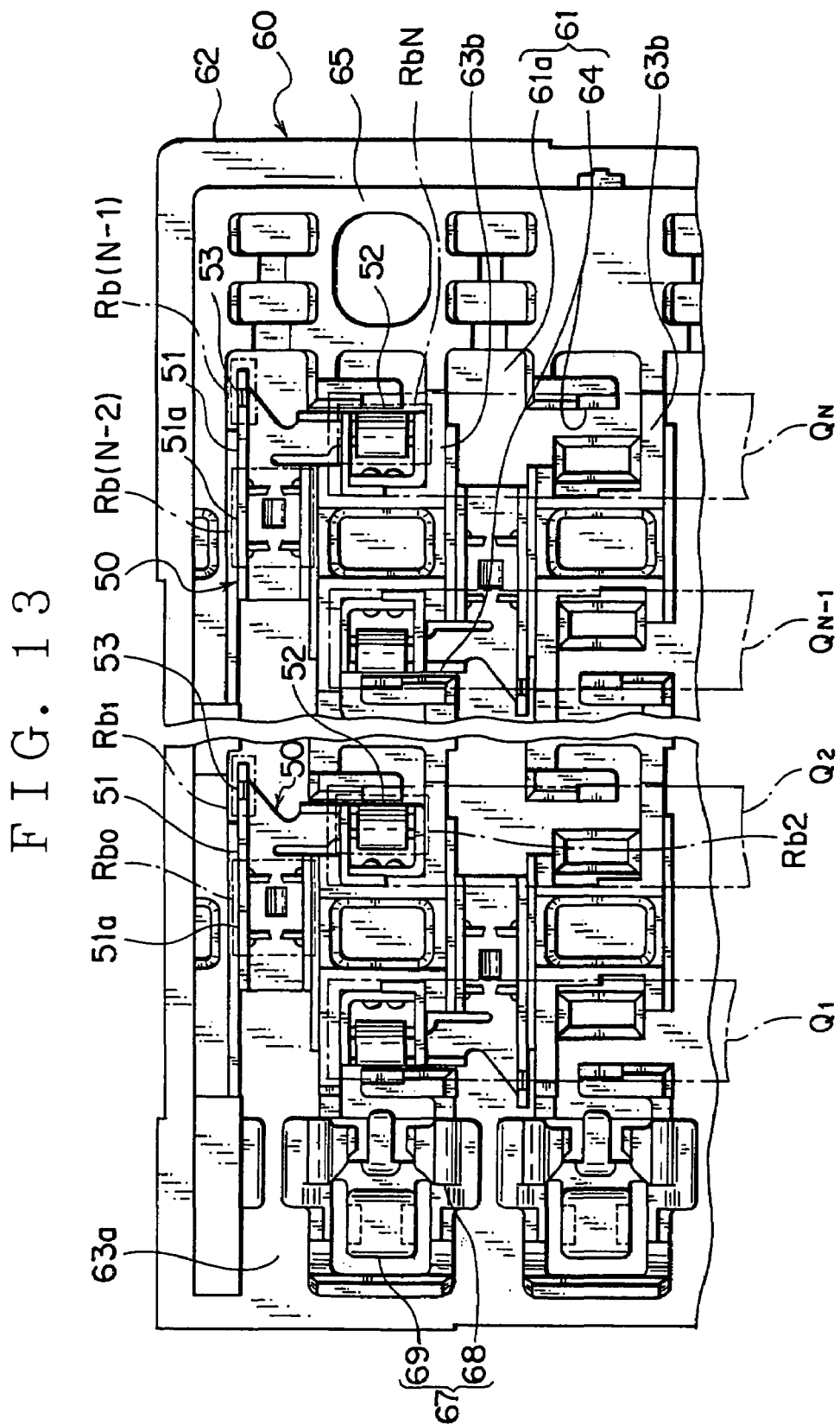
FIG. 13 illustrates another example of an image of a pressure-welding terminal for JB before the pressure-welding of a wire picked up by a CCD camera of the inspection apparatus shown in FIG. 8.

In this specification, as shown in FIGS. 12, 13, 17 and 18, the pressure-welding terminals 50 for JB, which is arranged along the direction of arranging the wire receiving grooves in parallel, is called as the pressure-welding terminals 50 for JB in first line (surrounded by an alternate long and short dash line Q1 shown in FIG. 12), the pressure-welding terminals 50 for JB in second line (surrounded by an alternate long and short dash line Q2 shown in FIG. 12), - - - , the pressure-welding terminals 50 for JB in (N−1) line (surrounded by an alternate long and short dash line QN−1shown in FIG. 12), and the pressure-welding terminals 50 for JB in N line (surrounded by an alternate long and short dash line QN shown in FIG. 12) when calling from a position near to the wire fixing part 67. In this regard, out of the pressure-welding terminals 50 for JB arranged along the direction, in which the wire receiving grooves 61 are arranged in parallel with each other, the pressure-welding terminals 50 for JB in odd line and that in even line are mounted on the pressure-welding plate 60 in a manner that the positional relationship between the wire connecting part 51 and the electric contact 52 is reversed with each other.

The pressure-welding terminals 50 for JB are mounted on the groove body 61a of the pressure-welding plate 60 and the receiving space 64. At this time, the pressure-welding terminal 50 for JB is brought close to the base wall 63a and mounted on the plate body 62. The locking piece 58 locks up the inner surface of the partition wall 63b, then the pressure-welding terminals 50 for JB is received in the wire-receiving groove 61, thereby being fixed to the pressure-welding plate 60.

Then, the wire 6 is pressure-welded to the pressure-welding terminals 50 for JB, which is received in the groove body 61a and the receiving space 64. At this time, the wire 6 is press-fit between the pressure-welding blades 54a and 54b of the wire connecting part 51 and received into the wire-receiving groove 61. The pressure-welding terminals 50 for JB, to which the same wire 6 is pressure-welded, electrically connects with each other.

On such a state, the pressure-welding plates 60 are laminated to each other in a manner that the plate bodies 62 are arranged in parallel with each other leaving a space therebetween. Then, the pressure-welding plates 60 are brought close to each other and the locking projection 66 engages with the lock receiving projection, thereby each pressure-welding plate 60 is fixed. The connection bar is inserted into the predetermined hole and the cylinder hole of the electric contact 52, thereby the pressure-welding plates 60 constitute a control panel.

The control panel connects the wires 6, which are pressure-welded to the pressure-welding terminals 50 for JB, according to a predetermined pattern by selecting a position where the pressure-welding terminal 50 for JB is arranged on the base wall 63a and a position where the connection bar is inserted.

The inspection apparatus 100 inspects whether or not the pressure-welding terminals 50 for JB are mounted on the predetermined places on the pressure-welding plates 60 as well as the quality of the pressure-welding terminals 50 for JB thus mounted. Before the wire 6 is pressure-welded, the inspection apparatus 100 inspects the outside appearance of the electric contact 5 of the pressure-welding terminal 50 for JB, the pressure-welding part 51a, and the caulking piece 53.

In addition, the inspection apparatus 100 inspects whether or not the wire 60 is pressure-welded to the pressure-welding part 51a of the pressure-welding terminal 50 for JB mounted on the pressure-welding plate 60 and whether or not the caulking piece 53 securely caulks the wire 60. After the wire 6 is pressure-welded, the inspection apparatus 100 inspects the outside appearance of the pressure-welding part 51a of the pressure-welding terminal 50 for JB and the caulking piece 53.

In this preferred embodiment, the pressure-welding plate 60 to be inspected is placed on the surface 9a of the inspection table 9. The illumination lamp 4 emits the light to the pressure-welding plate 60 to be inspected placed on the inspection table 9. The CCD camera 5 picks up an image of the pressure-welding plate 60 to be inspected placed on the inspection table 9. The CCD camera 5 picks up an image of the pressure-welding terminal 50 for JB mounted on the pressure-welding plate 60 and that of the wire 6 pressure-welded to the pressure-welding terminal 50 for JB.

The input device 24 is used to input the followings to the image-processing device 7: the number of the pressure-welding plates 60 to be inspected; the positions of sections to be inspected (explained later on) Ra0, Ra1, Ra2, - - - , Ra(N−2), Ra(N−1), RaN, Rb0, Rb1, Rb2, - - - , Rb(N−2), Rb(N−1), RbN, Rc0, Rc1, Rc2, - - - , Rc(N−2), Rc(N−1), RcN, Rd0, Rd1, Rd2, - - - , Rd(N−2), Rd(N−1), and RdN; and comparison data 3*a*, 3*b*, 3*c* and 3*d* (shown in FIGS. 10, 11, 15 and 16).

The comparison data 3*a*, 3*b*, 3*c* and 3*d* show portions of the pressure-welding terminals 50 for JB, which should be in each sections Ra0, Ra1, Ra2, - - - , Ra(N−2), Ra(N−1), RaN, Rb0, Rb1, Rb2, - - - , Rb(N−2), Rb(N−1), RbN, Rc0, Rc1, Rc2, - - - , Rc(N−2), Rc(N−1), RcN, Rd0, Rd1, Rd2, - - - , Rd(N−2), Rd(N−1), and RdN when the proper mounting, the proper pressure-welding and the proper caulking are carried out. In this preferred embodiment, the electric contact 52, the pressure-welding part 51*a* and the caulking piece 53 are used as the portions of the pressure-welding terminals 50 for JB.

The display device 25 displays the quality of the operating state of the inspection apparatus 100 and the quality of the pressure-welding terminals 50 for JB inspected. The output device 26 outputs the quality of the pressure-welding terminals 50 for JB inspected by the inspection apparatus 100 and so on.

The image-processing device 7 corresponds to both of the extraction means and the second extraction means, which are described in this specification. The image-processing device 7 takes in and stores the images of the pressure-welding plates picked up by the CCD camera 5. In this connection, these images are digital images, in which each optical power thereof is shown in 256 grades, in each pixel of the CCD camera 5 arranged in two dimensions.

The image-processing device 7 stores positions of the sections to be inspected of the images from the CCD camera 5, Ra0, Ra1, Ra2, - - - , Ra(N−2), Ra(N−1), RaN, Rb0, Rb1, Rb2, - - - , Rb(N−2), Rb(N−1), RbN, Rc0, Rc1, Rc2, - - - , Rc(N−2), Rc(N−1), RcN, Rd0, Rd1, Rd2, - - - , Rd(N−2), Rd(N−1), and RdN (that is, the sections surrounded by each alternate long and short dash line in FIGS. 12, 13, 17 and 18). The positions of the sections to be inspected, Ra0, Ra1, Ra2, - - - , Ra(N−2), Ra(N−1), RaN, Rb0, Rb1, Rb2, - - - , Rb(N−2), Rb(N−1), RbN, Rc0, Rc1, Rc2, - - - , Rc(N−2), Rc(N−1), RcN, Rd0, Rd1, Rd2, - - - , Rd(N−2), Rd(N−1), and RdN are input from the input device 24 to the image-processing device 7.

The sections to be inspected Ra0, Ra1, Ra2, - - - , Ra(N−2), Ra(N−1), RaN, Rb0, Rb1, Rb2, - - - , Rb(N−2), Rb(N−1), and RbN are the sections including one of the electric contact 52, the pressure-welding part 51*a* and the caulking piece 53. The sections to be inspected Ra0, Ra1, Ra2, - - - , Ra(N−2), Ra(N−1), and RaN are the sections of each portion of the pressure-welding terminal 50 for JB in odd line before the pressure-welding of the wire 6. The sections to be inspected Rb0, Rb1, Rb2, - - - , Rb(N−2), Rb(N−1), and RbN are the sections of each portion of the pressure-welding terminal 50 for JB in even line before the pressure-welding of the wire 6.

The sections to be inspected Rc0, Rc1, Rc2, - - - , Rc(N−2), Rc(N−1), RcN, Rd0, Rd1, Rd2, - - - , Rd(N−2), Rd(N−1), and RdN are the sections including the pressure-welding part 51*a* of the pressure-welding terminal 50 for JB or the caulking piece 53. The sections to be inspected Rc0, Rc1, Rc2, - - - , Rc(N−2), Rc(N−1), and RcN are the sections of each portion of the pressure-welding terminal 50 for JB in odd line after the pressure-welding of the wire 6. The sections to be inspected Rd0, Rd1, Rd2, - - - , Rd(N−2), Rd(N−1), and RdN are the sections of each portion of the pressure-welding terminal 50 for JB in even line after the pressure-welding of the wire 6.

The image-processing device 7 stores the image consulting data 2*a* shown in FIG. 9 and the second image consulting data 2*b* shown in FIG. 14. The image consulting data 2*a* stores a plurality of the images of the electric contact 52 of the non-defective pressure-welding terminal 50 for JB in odd line before the pressure-welding of the wire 6. The image consulting data 2*a* stores a plurality of the images of the pressure-welding part 51*a* of the non-defective pressure-welding terminal 50 for JB in odd line before the pressure-welding of the wire 6. The image consulting data 2*a* stores a plurality of the images of the caulking piece 53 of the non-defective pressure-welding terminal 50 for JB in odd line before the pressure-welding of the wire 6.

The image consulting data 2*a* stores a plurality of the images of the electric contact 52 of the non-defective pressure-welding terminal 50 for JB in even line before the pressure-welding of the wire 6. The image consulting data 2*a* stores a plurality of the images of the pressure-welding part 51*a* of the non-defective pressure-welding terminal 50 for JB in even line before the pressure-welding of the wire 6. The image consulting data 2*a* stores a plurality of the images of the caulking piece 53 of the non-defective pressure-welding terminal 50 for JB in even line before the pressure-welding of the wire 6.

Thus, the image consulting data 2*a* stores a plurality of the images of the electric contact 52, the pressure-welding part 51*a* and the caulking piece 53 of the non-defective pressure-welding terminal 50 for JB in odd line. The image consulting data 2*a* also stores a plurality of the images of the electric contact 52, the pressure-welding part 51*a* and the caulking piece 53 of the non-defective pressure-welding terminal 50 for JB in even line. Among these images of the same portion of the pressure welding terminal 50 for JB, the influences of the external light and so on are different from each other.

The second image consulting data 2*b* stores a plurality of the images of the caulking piece 53 of the non-defective pressure-welding terminal 50 for JB in odd line after the pressure-welding of the wire 6. The image consulting data 2*b* stores a plurality of the images of the pressure-welding part 51*a* of the non-defective pressure-welding terminal 50 for JB in odd line after the pressure-welding of the wire 6. The second image consulting data 2*b* stores a plurality of the images of the caulking piece 53 of the non-defective pressure-welding terminal 50 for JB in even line after the pressure-welding of the wire 6. The image consulting data 2*b* stores a plurality of the images of the pressure-welding part 51*a* of the non-defective pressure-welding terminal 50 for JB in eve line after the pressure-welding of the wire 6.

Thus, the second image consulting data 2*b* stores a plurality of the images of the caulking piece 53 and the pressure-welding part 51*a* of the non-defective pressure-welding terminal 50 for JB in odd line. The second image consulting data 2*b* also stores a plurality of the images of the caulking piece 53 and the pressure-welding part 51*a* of the non-defective pressure-welding terminal 50 for JB in even line. Among these images of the same portion of the pressure welding terminal 50 for JB, the influences of the external light and so on are different from each other.

The image-processing device 7 stores the comparison data 3a, 3b, 3c and 3d. The comparison data 3a shown in FIG. 10 show portions of the pressure-welding terminals 50 for JB before the pressure-welding of the wire 6, which should be in each sections Ra0, Ra1, Ra2, - - -, Ra(N−2), Ra(N−1), and RaN when the proper mounting, the proper pressure-welding and the proper caulking are carried out. The comparison data 3b shown in FIG. 11 show portions of the pressure-welding terminals 50 for JB before the pressure-welding of the wire 6, which should be in each sections Rb0, Rb1, Rb2, - - -, Rb(N−2), Rb(N−1), and RbN when the proper mounting, the proper pressure-welding and the proper caulking are carried out.

The comparison data 3c shown in FIG. 15 show portions of the pressure-welding terminals 50 for JB after the pressure-welding of the wire 6, which should be in each sections Rc0, Rc1, Rc2, - - -, Rc(N−2), Rc(N−1), and RcN when the proper mounting, the proper pressure-welding and the proper caulking are carried out. The comparison data 3d shown in FIG. 16 show portions of the pressure-welding terminals 50 for JB after the pressure-welding of the wire 6, which should be in each sections Rd0, Rd1, Rd2, - - -, Rd(N−2), Rd(N−1), and RdN when the proper mounting, the proper pressure-welding and the proper pressure-welding and the proper caulking are carried out.

On the basis of the comparison data 3a, 3b, 3c and 3d, the image-processing device 7 compares each image of the sections to be inspected Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN with the images stored in the image consulting data 2a or the second image consulting data 2b.

That is, the image-processing device 7 compares the images of the sections to be inspected Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN actually picked up by the CCD camera 5 with the images, which are stored in the image consulting data 2a or the second image consulting data 2b, of the portions of the pressure-welding terminals 50 for JB, which should be in each sections Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN when the proper mounting, the proper pressure-welding and the proper caulking are carried out.

For example, the image-processing device 7 compares an image of the section Ra0 to be inspected shown in FIG. 12 picked up by the CCD camera 5 with a plurality of the images stored in the image consulting data 2a of the electric contact 52 in odd line, which should be in the section Ra0 when the proper mounting, the proper pressure-welding and the proper caulking are carried out. For example, the image-processing device 7 compares an image of the section Rb0 to be inspected shown in FIG. 13 picked up by the CCD camera 5 with a plurality of the images stored in the image consulting data 2a of the pressure-welding part 51a in even line, which should be in the section Rb0 when the proper mounting, the proper pressure-welding and the proper caulking are carried out.

Figure 17:
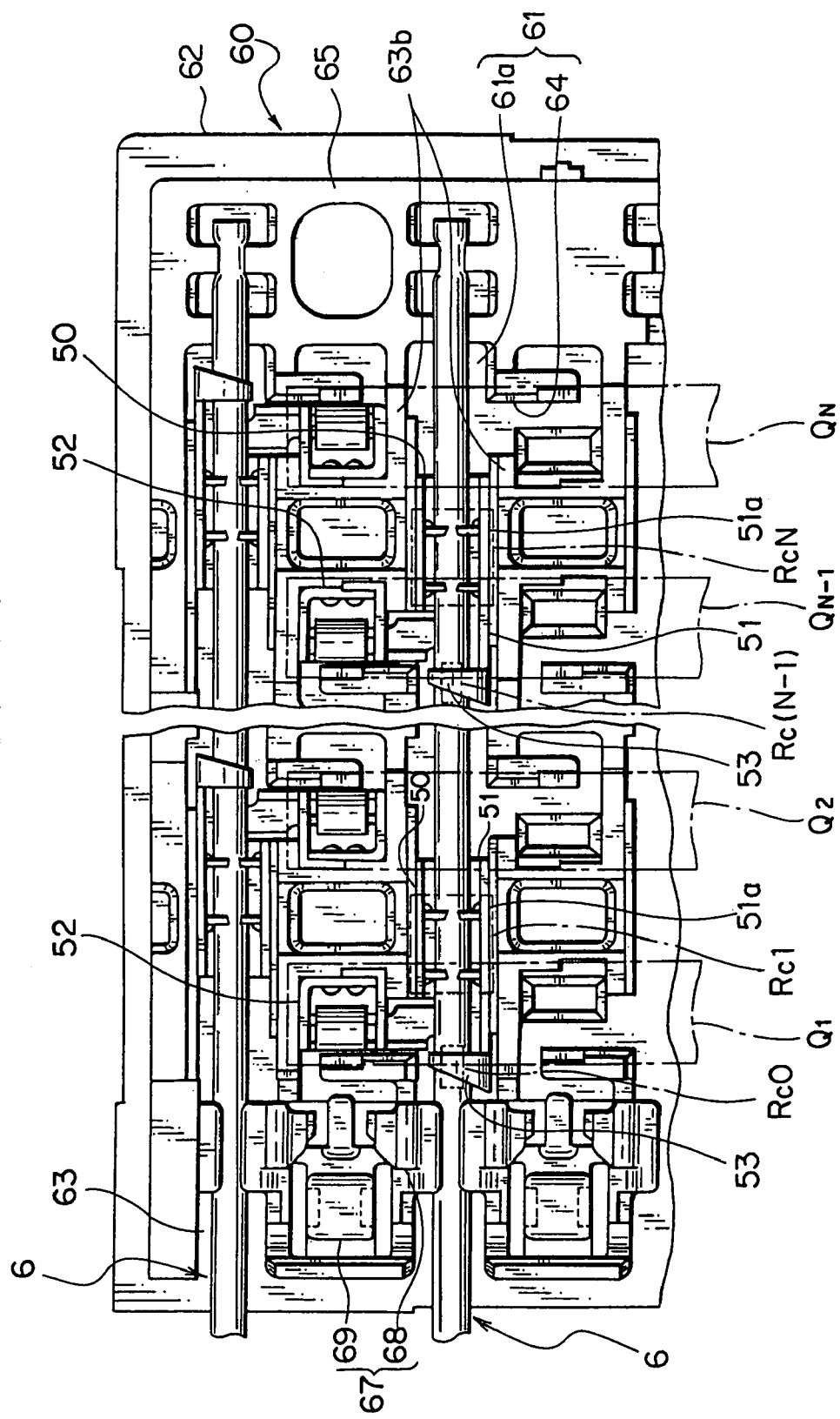
FIG. 17 illustrates one example of an image of a pressure-welding terminal for JB after the pressure-welding of a wire picked up by a CCD camera of the inspection apparatus shown in FIG. 8.
Figure 18:
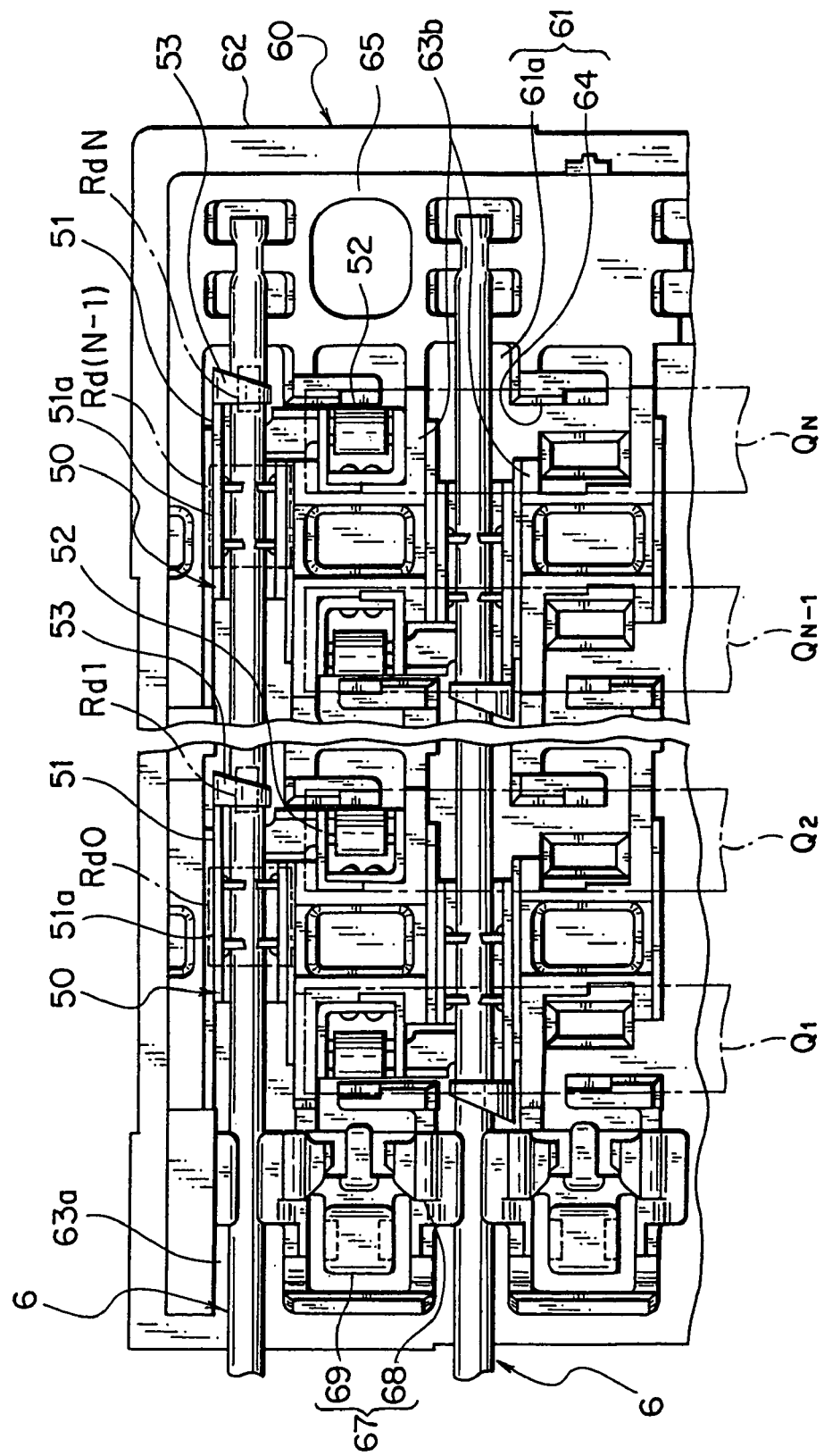
FIG. 18 illustrates another example of an image of a pressure-welding terminal for JB after the pressure-welding of a wire picked up by a CCD camera of the inspection apparatus shown in FIG. 8.

For example, the image-processing device 7 compares an image of the section Rc0 to be inspected shown in FIG. 17 picked up by the CCD camera 5 with a plurality of the images stored in the second image consulting data 2b of the caulking piece 53 in odd line, which should be in the section Rc0 when the proper mounting, the proper pressure-welding and the proper caulking are carried out. For example, the image-processing device 7 compares an image of the section Rd0 to be inspected shown in FIG. 18 picked up by the CCD camera 5 with a plurality of the images stored in the second image consulting data 2b of the pressure-welding part 51a in even line, which should be in the section Rd0 when the proper mounting, the proper pressure-welding and the proper caulking are carried out.

When the image-processing device 7 compares the images of the sections to be inspected Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN actually picked up by the CCD camera 5 with the images, which are stored in the image consulting data 2a or the second image consulting data 2b, of the portions of the pressure-welding terminals 50 for JB, which should be in each sections Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN when the proper mounting, the proper pressure-welding and the proper caulking are carried out, first the normalization processing is carried out. Then, on the basis of a known method of correlation, a correlation value indicating the degree of coincidence between the two images to be compared with each other described above is computed. Then, an image having the highest degree of coincidence, that is, the highest correlation value is extracted from the images stored in the image consulting data 2a or the second image consulting data 2b. The image having the highest correlation value is an image most analogous to the image picked up by the CCD camera 5.

Thus, the image-processing device 7 extracts an image most analogous to the image of the sections to be inspected, Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN picked up by the CCD camera 5 from a plurality of the images, stored in the image consulting data 2a or the second image consulting data 2b, of the portion of the pressure-welding terminal 50 for JB, which should be in each section Ra0, Ra1, Ra2, - - -, Ra(N−2), Ra(N−1), RaN, Rb0, Rb1, Rb2, - - -, Rb(N−2), Rb(N−1), RbN, Rc0, Rc1, Rc2, - - -, Rc(N−2), Rc(N−1), RcN, Rd0, Rd1, Rd2, - - -, Rd(N−2), Rd(N−1), and RdN.

The control device 8 controls the inspection apparatus 100. The control device 8 corresponds to both of the judgment means and the second judgment means, which are described in this specification. When the correlation value of the image, stored in the image consulting data 2a or the second image consulting data 2b, most analogous to the image picked up by the CCD camera 5 is equal to or higher than a predetermined threshold, the control device 8 judges that there is no abnormality for the portion of the pressure-welding terminal 50 for JB. That is, when the correlation value of the image, stored in the image consulting data 2a or the second image consulting data 2b, most analogous to the image picked up by the CCD camera 5 is equal to or higher than a predetermined threshold, the control device 8 judges the pressure-welding terminal 50 for JB to be non-defective.

On the other hand, when the correlation value of the image, stored in the image consulting data 2a or the second image consulting data 2b, most analogous to the image picked up by the CCD camera 5 is lower than a predetermined threshold, the control device 8 judges that there is an abnormality for the portion of the pressure-welding terminal 50 for JB. That is, when the correlation value of the image, stored in the image consulting data 2a or the second image consulting data 2b, most analogous to the image picked up by the CCD camera 5 is lower than a predetermined threshold, the control device 8 judges the pressure-welding terminal 50 for JB to be defective.

If all the pressure-welding terminals 50 for JB mounted on the pressure-welding plate 60 are non-defective and the quality of the pressure-welding state of the wire 6 to all the pressure-welding terminals 50 for JB is good, the control device 8 outputs that all the pressure-welding terminals 50 for JB are non-defective to the output device 26. If there is a defective among the pressure-welding terminals 50 for JB mounted on the pressure-welding plate 60, the control device 8 outputs a defective portion of such a defective terminal, in other words, a section Ra0, Ra1, Ra2, - - - , Ra(N−2), Ra(N−1), RaN, Rb0, Rb1, Rb2, - - - , Rb(N−2), Rb(N−1), RbN, Rc0, Rc1, Rc2, - - - , Rc(N−2), Rc(N−1), RcN, Rd0, Rd1, Rd2, - - - , Rd(N−2), Rd(N−1), or RdN including such a defective portion, to the output device 26.

Figure 21:
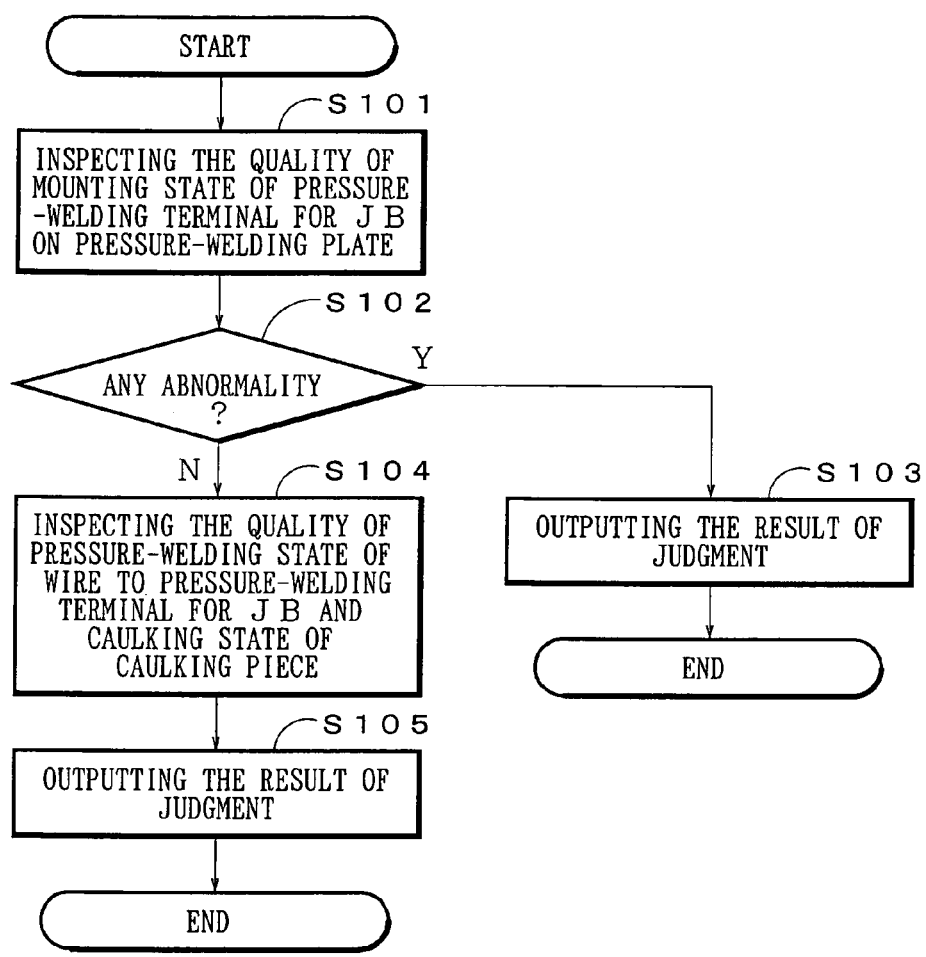
FIG. 21 is a flow chart illustrating an inspection flow by the inspection apparatus shown in FIG. 8.

Upon inspecting the pressure-welding terminal 50 for JB mounted on the pressure-welding plate 60, the inspection apparatus 100 according to this preferred embodiment first inspects the quality of the mounting state of the pressure-welding terminal 50 for JB onto the pressure-welding plate 60 in step S101 shown in FIG. 21.

Upon inspecting the quality of the mounting state of the pressure-welding terminal 50 for JB onto the pressure-welding plate 60, in step S11 shown in FIG. 22, first the control device 8 controls the driving control section 29 to make the CCD camera 5 face the pressure-welding plate 60. The CCD camera 5 picks up an image of the pressure-welding terminal 50 for JB mounted on the pressure-welding plate 60, then outputs the picked image to the image-processing device 7.

The image-processing device 7 stores the image from the CCD camera 5 for a while, then advancing to step S12. In step S11, the image, which is picked up by the CCD camera 5 and stored in the image-processing device 7 for a while, is a digital image in two dimensions, in which the optical power is shown in 256 grades thereof.

In step S12, the image-processing device 7 first extracts the images of the sections to be inspected Ra0, Ra1, Ra2, - - - , Ra(N−2), Ra(N−1), and RaN in odd line from the images from the CCD camera 5. On the basis of the comparison data 3a, the image-processing device 7 compares the images of the sections to be inspected Ra0, Ra1, Ra2, - - - , Ra(N−2), Ra(N−1), and RaN with the images, which are stored in the image consulting data 2a, of the portions of the pressure-welding terminals 50 for JB, which should be in each sections Ra0, Ra1, Ra2, - - - , Ra(N−2), Ra(N−1), and RaN when the proper mounting, the proper pressure-welding and the proper caulking are carried out.

In addition, in step S12, the image-processing device 7 extracts the images of the sections to be inspected Rb0, Rb1, Rb2, - - - , Rb(N−2), Rb(N−1), and RbN in even line from the images from the CCD camera 5. On the basis of the comparison data 3b, the image-processing device 7 compares the images of the sections to be inspected Rb0, Rb1, Rb2, - - - , Rb(N−2), Rb(N−1), and RbN with the images, which are stored in the image consulting data 2a, of the portions of the pressure-welding terminals 50 for JB, which should be in each sections Rb0, Rb1, Rb2, - - - , Rb(N−2), Rb(N−1), and RbN when the proper mounting, the proper pressure-welding and the proper caulking are carried out, then advancing to step S13.

In step S13, the image-processing device 7 extracts an image most analogous to each image of the sections to be inspected, Ra0, Ra1, Ra2, - - - , Ra(N−2), Ra(N−1), RaN, Rb0, Rb1, Rb2, - - - , Rb(N−2), Rb(N−1), and RbN from the images stored in the image consulting data 2a. The image-processing device 7 outputs the correlation value of the most analogous image to the control device 8, then advancing to step S14.

In step S14, the image-processing device 7 judges whether or not the correlation value of the image most analogous to each image of the sections to be inspected, Ra0, Ra1, Ra2, - - - , Ra(N−2), Ra(N−1), RaN, Rb0, Rb1, Rb2, - - - , Rb(N−2), Rb(N−1), and RbN has been computed. If judged computed, the system advances to step S15. If judged not computed, the system returns back to step S12 and starts again from step S12.

In step S15, the control device 8 judges whether or not the correlation value of the image most analogous to each image of the sections to be inspected, Ra0, Ra1, Ra2, - - - , Ra(N−2), Ra(N−1), RaN, Rb0, Rb1, Rb2, - - - , Rb(N−2), Rb(N−1), and RbN is equal to or higher than the predetermined threshold. If judged equal to or higher, the control device 8 judges each portion of the pressure-welding terminal 50 for JB to be non-defective, that is, judges the quality of the mounting state of the pressure-welding terminal 50 for JB onto the pressure-welding plate 60 to be good. On the other hand, if judged less, the control device 8 judges each portion of the pressure-welding terminal 50 for JB to be defective, that is, judges the quality of the mounting state of the pressure-welding terminal 50 for JB onto the pressure-welding plate 60 to be no good.

Thus, in step S15, the quality of the mounting state of the pressure-welding terminal 50 for JB onto the pressure-welding plate 60 is judged on the basis of the correlation value. The control device 8 outputs the result of the judgment to the output device 26.

When there is a pressure-welding terminal 50 for JB, the mounting state of which onto the pressure-welding plate 60 is no good, the system advances to step S103 by way of step S102 shown in FIG. 21. In step S103, the output device 26 outputs the result of the judgment judged by the control device 8 with printing it out and records in the recording medium. On the other hand, when the mounting state of all the pressure-welding terminals 50 for JB onto the pressure-welding plate 60 is good, the system advances to step S104 by way of step S102 shown in FIG. 21. Then, the wire 6 is pressure-welded to each pressure-welding terminals 50 for JB.

In step S104, the quality of the pressure-welding state (fixing state) of the wire 6 to the pressure-welding terminals 50 for JB mounted on the pressure-welding plate 60 is inspected. Upon the inspection, in step S21 shown in FIG. 23, first the control device 8 controls the driving control section 29 to make the CCD camera 5 face the pressure-welding plate 60. The CCD camera 5 picks up an image of the pressure-welding terminal 50 for JB mounted on the pressure-welding plate 60, then outputs the picked image to the image-processing device 7.

The image-processing device 7 stores the image from the CCD camera 5 for a while, then advancing to step S22. In step S21, the image, which is picked up by the CCD camera 5 and stored in the image-processing device 7 for a while, is a digital image in two dimensions, in which the optical power is shown in 256 grades thereof.

In step S22, the image-processing device 7 first extracts the images of the sections to be inspected Rc0, Rc1, Rc2, - - -, Rc(N−2), Rc(N−1), and RcN in odd line from the images from the CCD camera 5. On the basis of the comparison data 3*c*, the image-processing device 7 compares the images of the sections to be inspected Rc0, Rc1, Rc2, - - -, Rc(N−2), Rc(N−1), and RcN with a plurality of the images, which are stored in the second image consulting data 2*b*, of the portions of the pressure-welding terminals 50 for JB, which should be in each sections Rc0, Rc1, Rc2, - - -, Rc(N−2), Rc(N−1), and RcN when the proper mounting, the proper pressure-welding and the proper caulking are carried out.

In addition, in step S22, the image-processing device 7 extracts the images of the sections to be inspected Rd0, Rd1, Rd2, - - -, Rd(N−2), Rd(N−1), and RdN in even line from the images from the CCD camera 5. On the basis of the comparison data 3*d*, the image-processing device 7 compares the images of the sections to be inspected Rd0, Rd1, Rd2, - - -, Rd(N−2), Rd(N−1), and RdN with the images, which are stored in the second image consulting data 2*b*, of the portions of the pressure-welding terminals 50 for JB, which should be in each sections Rd0, Rd1, Rd2, - - -, Rd(N−2), Rd(N−1), and RdN when the proper mounting, the proper pressure-welding and the proper caulking are carried out, then advancing to step S23.

In step S23, the image-processing device 7 extracts an image most analogous to each image of the sections to be inspected, Rc0, Rc1, Rc2, - - -, Rc(N−2), Rc(N−1), RcN, Rd0, Rd1, Rd2, - - -, Rd(N−2), Rd(N−1), and RdN from the images stored in the second image consulting data 2*b*. The image-processing device 7 outputs the correlation value of the most analogous image to the control device 8, then advancing to step S24.

In step S24, the image-processing device 7 judges whether or not the correlation value of the image most analogous to each image of the sections to be inspected, Rc0, Rc1, Rc2, - - -, Rc(N−2), Rc(N−1), RcN, Rd0, Rd1, Rd2, - - -, Rd(N−2), Rd(N−1), and RdN has been computed. If judged computed, the system advances to step S25. If judged not computed, the system returns back to step S22 and starts again from step S22.

In step S25, the control device 8 judges whether or not the correlation value of the image most analogous to each image of the sections to be inspected, Rc0, Rc1, Rc2, - - -, Rc(N−2), Rc(N−1), RcN, Rd0, Rd1, Rd2, - - -, Rd(N−2), Rd(N−1), and RdN is equal to or higher than the predetermined threshold. If judged equal to or higher, the control device 8 judges each portion of the pressure-welding terminal 50 for JB to be non-defective, that is, judges the quality of the pressure-welding state of the wire 6 to the pressure-welding terminal 50 for JB to be good. On the other hand, if judged less, the control device 8 judges each portion of the pressure-welding terminal 50 for JB to be defective, that is, judges the quality of the pressure-welding state of the wire 6 to the pressure-welding terminal 50 for JB to be no good.

Thus, in step S25, the quality of the pressure-welding state of the wire 6 to the pressure-welding terminal 50 for JB is judged on the basis of the correlation value. The control device 8 outputs the result of the judgment to the output device 26. In step S105, the output device 26 outputs the result of the judgment judged by the control device 8 with printing it out and records in the recording medium.

According to this preferred embodiment, a plurality of images of each portion of the pressure-welding terminal 50 for JB to be mounted on the pressure-welding plate 60 are stored in advance. An image most analogous to the image picked up by the CCD camera 5 is extracted from these stored images.

Therefore, an image analogous to the image of the pressure-welding terminal 50 for JB picked up by the CCD camera 5 may be included in the images stored in the image consulting data 2*a* or the second image consulting data 2*b* with high probability. That is, the degree of coincidence between the image picked up by the CCD camera 5 and the most analogous image stored in the image consulting data 2*a* or the second image consulting data 2*b*.

By comparing the most analogous image with the image picked up by the CCD camera 5, it is judged whether or not the quality of the mounting state of the pressure-welding terminal 50 for JB onto the pressure-welding plate 60 is good and whether or not the quality of the pressure-welding (fixing) state of the wire 6 to the pressure-welding terminal 50 for JB is good. A plurality of images of the pressure-welding terminal 50 for JB having the same item symbol are stored in the image consulting data 2*a* or the second image consulting data 2*b*, thereby an error in the detection judging a non-defective to be a defective can be prevented from occurring. Therefore, the quality of the mounting state of the pressure-welding terminal 50 for JB onto the pressure-welding plate 60 and the quality of the pressure-welding (fixing) state of the wire 6 to the pressure-welding terminal 50 for JB can be securely judged.

The method of normalization correlation is employed when the image most analogous to the image picked up by the CCD camera 5 is extracted from the images stored in the image consulting data 2*a* or the second image consulting data 2*b*. Thereby, the degree of coincidence between the images of the same portion of the pressure-welding terminal 50 for JB becomes higher compared to a case, in which images recorded in a binary condition are compared with each other. Therefore, the quality of the mounting state of the pressure-welding terminal 50 for JB onto the pressure-welding plate 60 and the quality of the pressure-welding (fixing) state of the wire 6 to the pressure-welding terminal 50 for JB can be securely judged.

In addition, the quality of the mounting state of the pressure-welding terminal 50 for JB onto the pressure-welding plate 60 is judged by using the images of the electric contact 52, the pressure-welding part 51*a* and the caulking piece 53. The quality of the pressure-welding (fixing) state of the wire 6 to the pressure-welding terminal 50 for JB is judged by using the images of the pressure-welding part 51*a* and the caulking piece 53. Therefore, the quality of the mounting state of the pressure-welding terminal 50 for JB onto the pressure-welding plate 60 and the quality of the pressure-welding (fixing) state of the wire 6 to the pressure-welding terminal 50 for JB can be more securely judged.

In the previous preferred embodiment, the non-defectiveness or defectiveness of the pressure-welding terminal 50 for JB is judged before and after the pressure welding of the wire 6. However, in this preferred embodiment, the non-defectiveness or defectiveness of the pressure-welding terminal 50 for JB is judged at least before or after the pressure welding of the wire 6.

Figure 24:
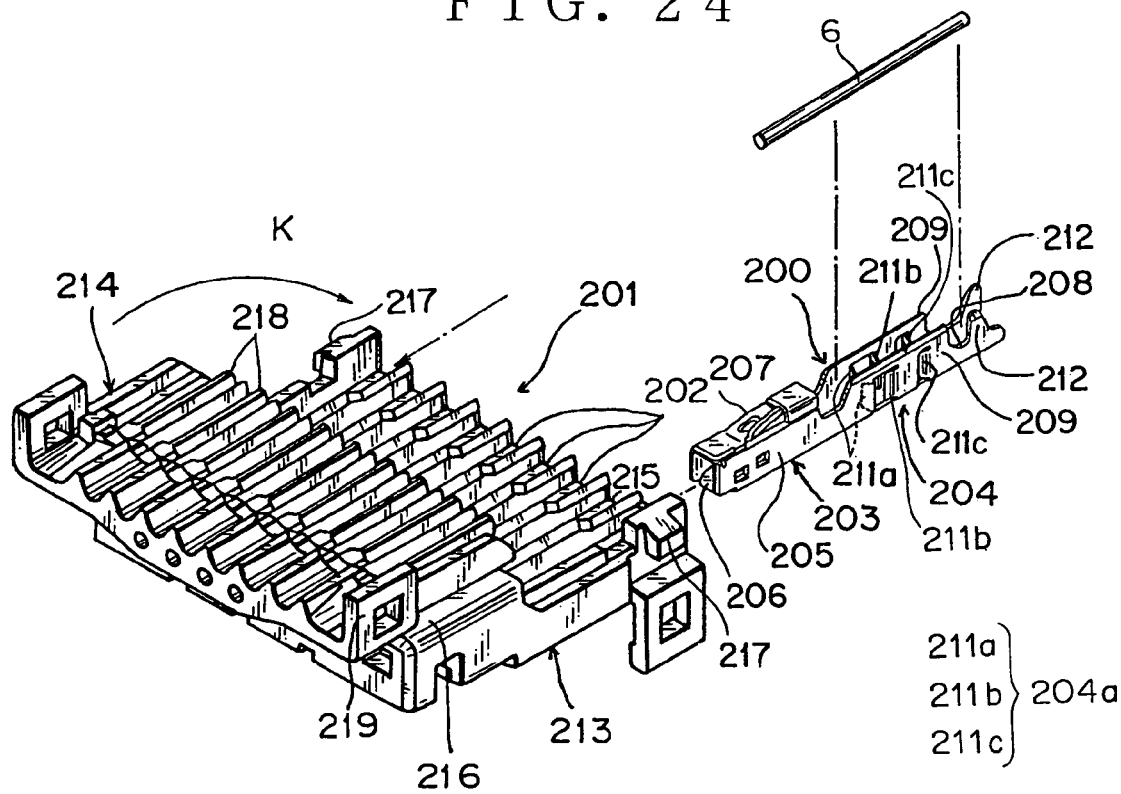
FIG. 24 is a perspective view illustrating another example of a pressure-welding terminal to be inspected by the inspection apparatus shown in FIG. 8 and a connector housing.

In the previous preferred embodiment, inspected is the pressure-welding plate 60, which can be mounted by arranging along the two directions, the length direction of the wire-receiving groove 61 and the direction, in which a plurality of the wire-receiving groove 61 are arranged to each other. However, in this preferred embodiment, inspected may be the quality of the pressure-welding terminal 200 arranged along only one direction in a connector housing 201 as shown in FIG. 24. The connector housing 201 corresponds to the insulator described in this specification. The pressure-welding terminal 200 corresponds to the terminal fittings described in this specification. A terminal-receiving groove 202 (explained later on) corresponds to the mount described in this specification. In addition, the pressure-welding terminal 200 corresponds to the electric part described in this specification.

The pressure-welding terminal 200 is made by bending an electrically conductive sheet metal and has the electric contact 203 and the wire-connecting part 204 as shown in FIG. 24.

The electric contact 203 has a cylindrical part 205, a resilient contact piece 206 for connecting to a male terminal (not shown in the figure) and a lance 207 for engaging with the connector housing 201. The cylindrical part 205 continues to a wall 208 and a side wall 209 (explained later on) of the wire-connecting part 204. The resilient contact piece 206 is formed in the cylindrical part 205 and urges a male terminal entered into the cylindrical part 205 toward the inner surface of the cylindrical part 205 so as to prevent the male terminal from coming out from the cylindrical part 205.

The lance 207 is formed in a band-shape and provided at the outer surface side of the cylindrical part 205. One end of the lance 207 continues to the cylindrical part 205 while an opposite end thereof can resiliently deform so as to be approached and to be parted from the cylindrical part 205. The lance 207 engages with the connector housing 201 so as to prevent the pressure-welding terminal 200 from coming out from the terminal-receiving groove 202.

The wire-connecting part 204 has a wall 208 on which the wire 6 is placed, a pair of side walls 209, a pressure-welding part 204a, and a pair of caulking pieces 212. The wall 208 is formed in a flat band plate-shape at the surface thereof. Each side wall 209 continues to both peripheries in the width direction of the wall 208. Each side wall 209 arises perpendicularly from the wall 208 and faces another side wall.

The pressure-welding part 204a has three pairs of pressure-welding blades 211a, 211b and 211c, each pair of which arises perpendicularly from the wall 208. A pair of the blades 211a protrudes in the direction approaching each other from the side wall 209. A pair of the blades 211a is arranged leaving a space therebetween. A pair of the blades 211a press fits the wire 6 therebetween so as to come into contact with the core of the wire 6 by cutting the coated part of the wire 6.

A pair of the blades 211b protrudes in the direction approaching each other from the side wall 209. A pair of the blades 211b is arranged leaving a space therebetween. A pair of the blades 211b press fits the wire 6 therebetween so as to come into contact with the core of the wire 6 by cutting the coated part of the wire 6. A pair of the blades 211c protrudes in the direction approaching each other from the side wall 209. A pair of the blades 211c is arranged leaving a space therebetween. A pair of the blades 211c press fits the wire 6 therebetween so as to come into contact with the core of the wire 6 by cutting the coated part of the wire 6. The three pairs of the blades 211a, 211b and 211c electrically connect with the wire 6. That is, the three pairs of the blades 211a, 211b and 211c are pressure-welded to the wire 6.

A pair of the caulking pieces 212 continues to both peripheries in the width direction of the wall 208. A pair of the caulking pieces 212 arises perpendicularly from the wall 208. A pair of the caulking pieces 212 faces each other leaving a space therebetween. The caulking piece 212 is bent facing the wall 208, thereby putting the wire 6 between the caulking piece 212 and the wall 208. That is, a pair of the caulking pieces caulk the wire 6. Thus, a pair of the caulking pieces 212 fixes the wire 6 to the wire-connecting part 204.

The connector housing 201 is made of electrically insulating synthetic resin. As shown in FIG. 24, the connector housing 201 has a terminal-receiving part 213 and a cover 214 connected to the terminal-receiving part 213 through a hinge.

The terminal-receiving part 213 has a rectangular plate 215, a plurality of terminal-receiving grooves 202, and a ceiling wall 216 facing the plate 215 leaving a space therebetween. The plate 215 has a locking groove and a locking arm (not shown in the figure) to prevent the pressure-welding terminal 200 inserted in the terminal-receiving groove 202 from coming out therefrom.

Each terminal-receiving groove 202 is formed extending in a linear shape with being recessed from the surface of the plate 215 and arranged in parallel. The pressure-welding terminal 200 is inserted into the terminal-receiving groove 202 along the length direction thereof.

The ceiling wall 216 is formed rectangular in the plan view thereof. The ceiling wall 216 exposes the wire-connecting part 204 of the pressure-welding terminal 200 received in the terminal-receiving groove 202 and covers the electric contact 203. The periphery apart from the ceiling wall 216 of the plate 215 is provided with an engaging projection 217 protruding toward the outside.

The cover 214 has a plurality of protruding stripes for holding the wire, which fit into the terminal-receiving groove 202 of the terminal-receiving part 213. The cover 214 has a cover locking arm 219 engaging with the engaging projection 217. The cover 214 is rotatable in relation to the terminal-receiving part 213 by a hinge (not shown in the figure) provided at the periphery of the ceiling wall 216.

Before the assembly, in the connector housing 201, the terminal-receiving groove 202 of the terminal-receiving part 213 is connected to the protruding stripe 218 of the cover 214 by a band (not shown in the figure) in a state that each opening is situated into the same direction. That is, the terminal-receiving part 213 is connected to the cover 214 by the band in a state that the cover 214 turns over in relation to the terminal-receiving part 213.

Upon the assembly, first the pressure-welding terminal 200 is inserted into the terminal-receiving groove 202 along the length direction thereof. The lance 207 engages with the connector housing 201 and the pressure-welding terminal 200 is fixed to (mounted in) the connector housing 201 in a state that the pressure-welding terminal 200 is received in the terminal-receiving groove 202. Thereafter, by using the inspection apparatus 100, the mounting state of the pressure-welding terminal 200 on the connector housing 201 is inspected. The wire 6 is press fit between the pressure-welding blades 211a, 211b and 211c. The caulking piece 212 is bent. The wire 6 is fixed to the pressure-welding terminal 200.

Thereafter, by using the inspection apparatus 100, the pressure-welding state (fixing state) of the wire 6 to the pressure-welding terminal 200 is inspected. If all the pressure-welding terminals 200 are non-defective, the band is removed and the cover 214 is rotated along arrow K shown in FIG. 24 around the hinge. The cover locking arm 219 engages with the engaging projection 217 so as to fix the terminal receiving part 213 and the cover 214 to each other.

Figure 25:
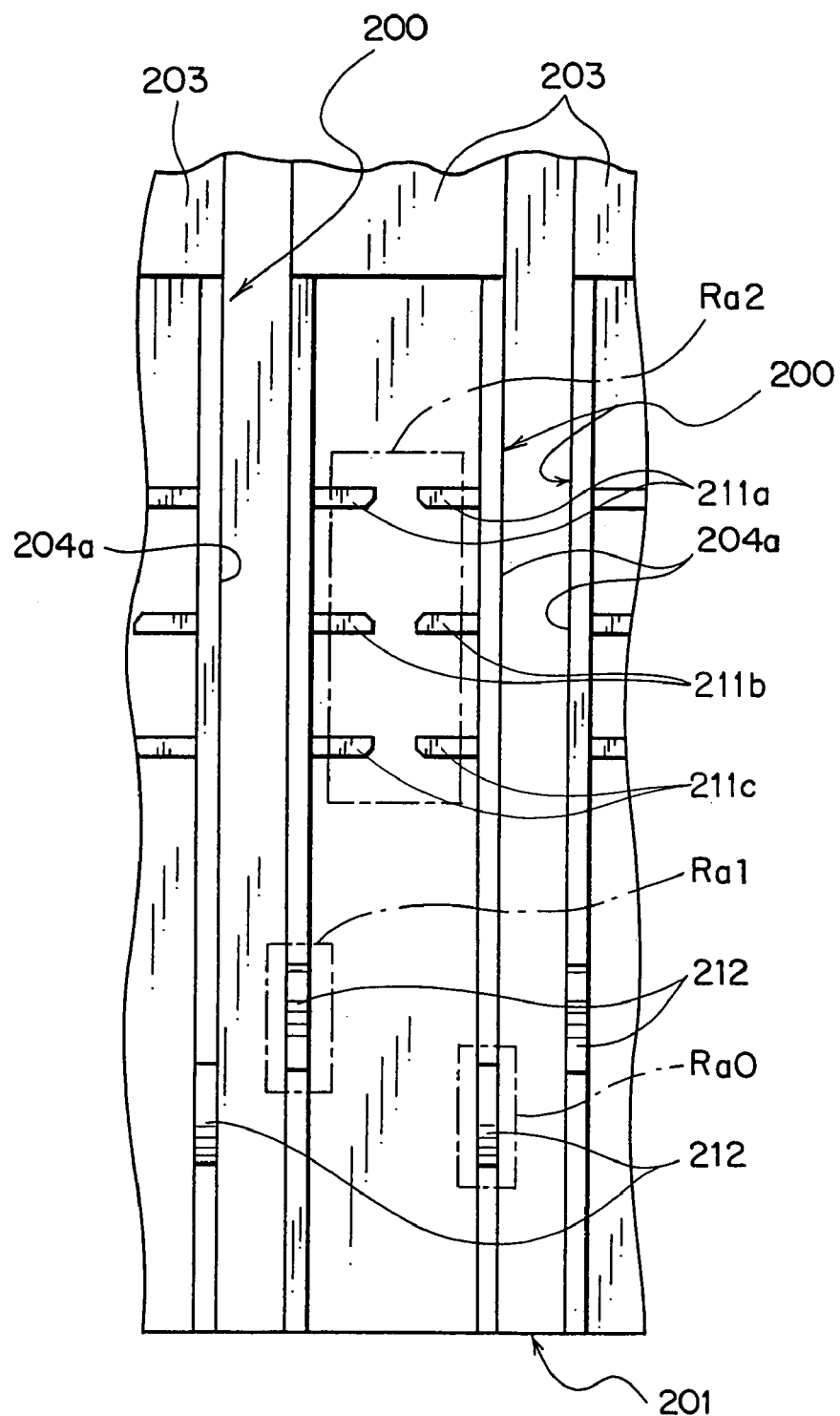
FIG. 25 is an illustration showing a state for inspection of the pressure-welding terminal shown in FIG. 24 and a connector housing before the pressure-welding of the wire.

When the mounting state of the pressure-welding terminal on the connector housing 201 is inspected, that is, when the pressure-welding terminal 200 is inspected before the pressure-welding of the wire 6, the image of the caulking piece 212 and the image of the pressure-welding part 204a are preferably used as shown by surrounding with alternate long and short dash lines Ra0, Ra1 and Ra2 in FIG. 25.

Figure 26:
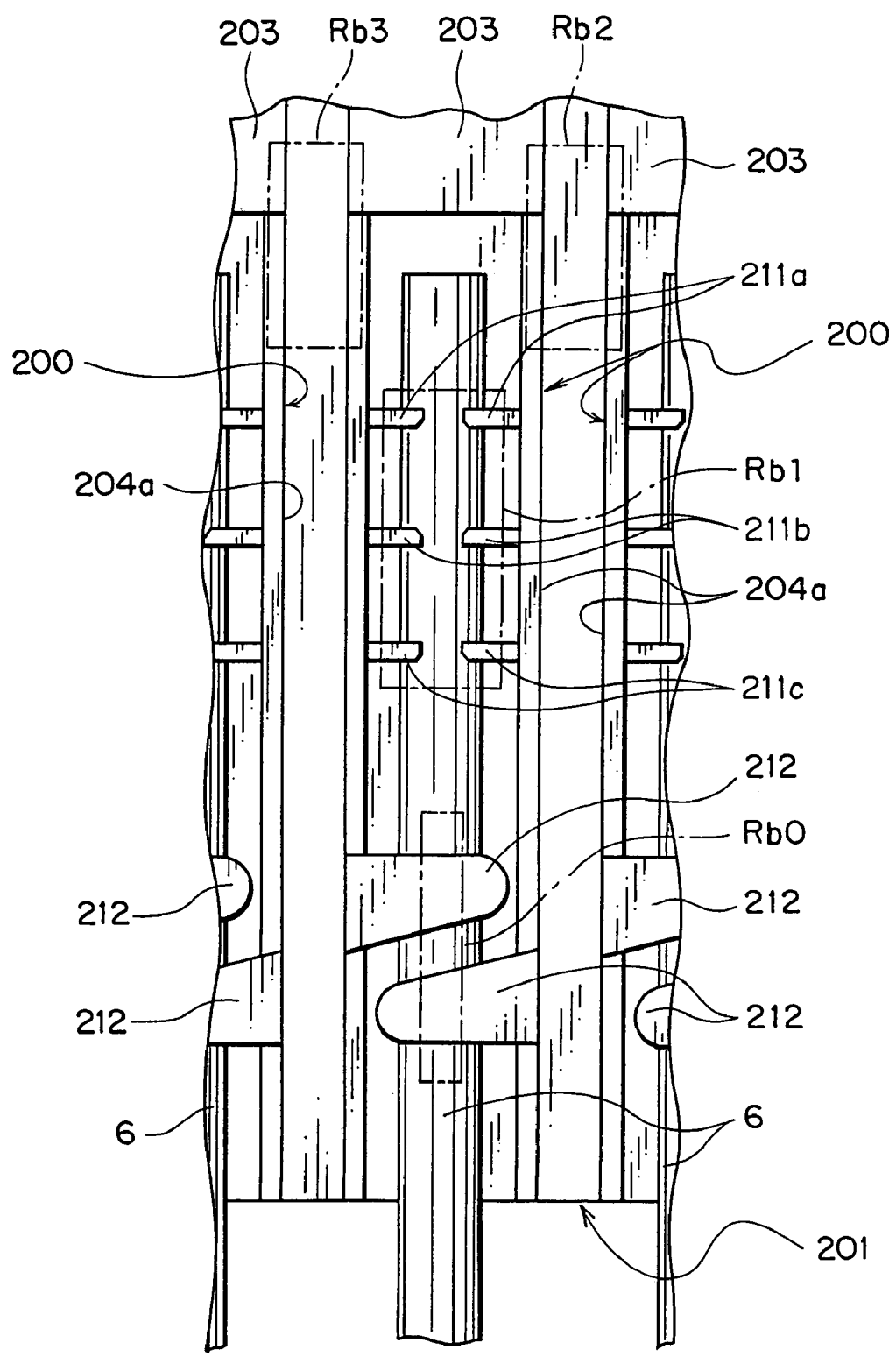
FIG. 26 is an illustration showing a state for inspection of the pressure-welding terminal shown in FIG. 24 and a connector housing after the pressure-welding of the wire.

When the pressure-welding state of the wire 6 to the pressure-welding terminal 200 mounted on the connector housing 201 is inspected, that is, when the pressure-welding terminal 200 is inspected after the pressure-welding of the wire 6, the image of the caulking piece 212, the image of the pressure-welding part 204a and the image of both sides of the end of the wire 6 are preferably used as shown by surrounding with alternate long and short dash lines Rb0, Rb1, Rb2 and Rb3 in FIG. 26. Particularly, both sides of the end of the wire 6 are preferably inspected in order to judge whether or not the core sticking out from the end of the wire 6 short-circuits to the other pressure-welding terminal 200 and so on.

By using the inspection apparatus according to the third preferred embodiment, the following inspection methods for inspecting an electric part can be obtained. One of them is an inspection method of an electric part comprising the steps of:

storing a plurality of images of the pressure-welding terminal 50 or 200 as a non-defective electric part in advance; and judging whether or not the quality of the mounting state of the pressure-welding terminal 50 or 200 on the pressure-welding plate 60 or the connector housing 201 is good and whether or not the quality of the pressure-welding state of the wire 6 to the pressure-welding terminal 50 or 200 is good, on the basis of the image of the pressure-welding terminal 50 or 200 to be inspected and a plurality of the images of the non-defective pressure-welding terminal 50 or 200, that is, judging whether or not the pressure-welding terminal 50 or 200 to be inspected is non-defective.

Another of them is an inspection method of an electric part comprising the steps of:

storing a plurality of images of pressure-welding terminal 50 or 200 as a non-defective electric part in advance;

comparing an image of pressure-welding terminal 50 or 200 to be inspected and a plurality of the images of a non-defective pressure-welding terminal 50 or 200;

extracting an image most analogous to the image of the pressure-welding terminal 50 or 200 to be inspected from a plurality of the images of a non-defective pressure-welding terminal 50 or 200; and judging whether or not the pressure-welding terminal 50 or 200 is non-defective on the basis of the most analogous image and the image of the pressure-welding terminal 50 or 200 to be inspected, that is, judging whether or not the pressure-welding terminal 50 or 200 is non-defective.

With the inspection methods described above, a plurality of images of non-defective pressure-welding terminal 50 or 200 are stored in advance. Thereby, an image analogous to the image of the pressure-welding terminal 50 or 200 to be inspected can be included in a plurality of the stored images of non-defective pressure-welding terminal 50 or 200 with high probability. Therefore, the degree of coincidence between the image of the pressure-welding terminal 50 or 200 to be inspected and an image most analogous to the image of the pressure-welding terminal 50 or 200 to be inspected out of a plurality of the stored images of non-defective pressure-welding terminal 50 or 200 becomes high. Consequently, an error of judging the quality of the pressure-welding terminal 50 or 200 can be prevented from occurring, that is, the quality of the pressure-welding terminal 50 or 200 can be securely judged.

In addition, the inspection apparatus 100 for inspecting the terminal fittings as shown in the third preferred embodiment of the present invention may be set up as an exclusive inspection apparatus as shown in the figure. The inspection apparatus 100 for inspecting the terminal fittings according to the present invention may be mounted on a known pressure-welding apparatus.

The aforementioned preferred embodiments are described to aid in understanding the present invention and variations may be made by one skilled in the art without departing from the spirit and scope of the present invention.

What is claimed is:

1. An inspection apparatus of an electric junction box having a plurality of mounts on which electric parts are mounted, for inspecting mounting state of the electric parts, said each electric part having a different mark on an outer surface thereof depending upon an item symbol thereof, the inspection apparatus comprising:

image pickup means for picking up an image including said mark of the electric part mounted on the mount;

extraction means for (1) storing image consulting data containing a plurality of images including said marks of the electric parts of all the item symbols to be mounted in the electric junction box as a subject of the inspection and normal data indicating the proper item symbols of the electric parts mounted on the corresponding mounts, and for (2) comparing the image including said mark of the electric part mounted on the mount picked up by the image pickup means and the image in the image consulting data, and for (3) extracting the item symbol of the electric part having the most analogous image from the images in the image consulting data; and judgment means for judging the quality of the mounting state of the electric parts on the mount by comparing the item symbol of the electric part having the most analogous image and said normal data.

2. The inspection apparatus of an electric junction box according to claim 1, wherein the image is a digital information, in which an optical power is indicated with a plurality of grades thereof, the extraction means compares the image including said mark of the electric part mounted on the mount in the electric junction box as a subject of the inspection and the image in the image consulting data by a method of normalization correlation so that the image having the highest correlation value obtained by the method of normalization correlation out of the images is set up to be said most analogous image, and the judgment means judges the quality of the mounting state of the electric parts on the mount by comparing the item symbol of the electric part of the image having the highest correlation value and said normal data.

3. An inspection apparatus of an electric junction box having a plurality of mounts on which electric parts are mounted, for inspecting mounting state of the electric parts, said each electric part having a different mark on an outer surface thereof corresponding to an item symbol thereof, the inspection apparatus comprising:

image pickup means for picking up an image, including said mark, of an electric part mounted on a mount to be inspected;

extraction means for (1) storing image consulting data including a plurality of item symbols wherein each of the item symbols corresponds to at least one of a plurality of images of non-defective electric parts, and storing normal data including a plurality of mounts to be inspected wherein each of the mounts to be inspected corresponds to at least one proper one of the item symbols, and for (2) comparing the image, including said mark, of the electric part mounted on the mount to be inspected picked up by the image pickup means and the images of the non-defective electric parts in the image consulting data by a method of normalization correlation, and for (3) extracting the highest correlation value out of the correlation values obtained by the method of normalization correlation; and judgment means for judging the quality of the mounting state of the electric parts on the mount in dependence upon the highest correlation value, the image consulting data, and the normal data.

4. The inspection apparatus of an electric junction box according to claim 2 or 3, wherein the judgment means adds the image including said mark of the electric part properly mounted on the mount, out of the electric parts judged improperly mounted on the mount, to the image consulting data.

5. An inspection apparatus of a terminal fittings for inspecting mounting state of the terminal fittings on an insulator, said terminal fittings being mounted at a mount to be inspected on the insulator and an electric wire being pressure-welded to the terminal fittings, the inspection apparatus comprising:

image pickup means for picking up an image of the terminal fittings mounted at the mount to be inspected on the insulator;

extraction means for (1) storing image consulting data including a plurality of item symbols wherein each of the item symbols corresponds to at least one of a plurality of images of non-defective terminal fittings mounted on the insulator, and storing normal data including a plurality of mounts to be inspected wherein each of the mounts to be inspected corresponds to at least one proper one of the item symbols, and for (2) comparing the image of the terminal fittings picked up by the image pickup means and the plurality of the images of non-defective terminal fittings in the image consulting data, and for (3) extracting an image most analogous to the image of the terminal fittings picked up by the image pickup means from the images in the image consulting data; and judgment means for judging the quality of the mounting state of the terminal fittings on the insulator in dependence upon the most analogous image, the image of the terminal fittings picked up by the image pickup means, the image consulting data, and the normal data.

6. The inspection apparatus of a terminal fittings according to claim 5, wherein the image is a digital information, in which an optical power is indicated with a plurality of grades thereof, the extraction means compares the image of the terminal fittings picked up by the image pickup means and a plurality of the images in the image consulting data by a method of normalization correlation so that the image having the highest correlation value obtained by the method of normalization correlation out of the images is set up to be said most analogous image, the judgment means judges the quality of the mounting state of the terminal fittings mounted at the mount to be inspected on the insulator to be good when the correlation value is equal to or higher than a predetermined threshold and the item symbol corresponding to the image of the terminal fittings picked up by the image pickup means corresponds, according to the normal data, to the proper item symbol for the mount to be inspected, and the judgement means judges the quality of the mounting state to be no good when the correlation value is lower than the predetermined threshold or when the item symbol corresponding to the image of the terminal fittings picked up by the image pickup means does not correspond, according to the normal data, to the proper item symbol for the mount to be inspected.

7. An inspection apparatus of a terminal fittings for inspecting pressure-welding state of an electric wire to the terminal fittings, said terminal fittings being mounted at a mount to be inspected on an insulator and the electric wire being pressure-welded to the terminal fittings, the inspection apparatus comprising:

image pickup means for picking up an image of the terminal fittings, to which the electric wire is pressure-welded, mounted at the mount to be inspected on the insulator;

extraction means for (1) storing image consulting data including a plurality of item symbols wherein each of the item symbols corresponds to at least one of a plurality of images of non-defective terminal fittings, to which the electric wire is pressure-welded, mounted on the insulator, and storing normal data including a plurality of mounts to be inspected wherein each of the mounts to be inspected corresponds to at least one proper one of the item symbols, and for (2) comparing the image of the terminal fittings, to which the electric wire is pressure-welded, picked up by the image pickup means and the plurality of images of non-defective terminal fittings, to which the electric wire is pressure-welded, in the image consulting data, and for (3) extracting an image most analogous to the image of the terminal fittings, to which the electric wire is pressure-welded, picked up by the image pickup means from the images in the image consulting data; and judgment means for judging the quality of the pressure-welding state of the electric wire to the terminal fittings, to which the electric wire is pressure-welded, mounted on the insulator in dependence upon the most analogous image, the image of the terminal fittings, to which the electric wire is pressure-welded, mounted on the insulator picked up by the image pickup means, the image consulting data, and the normal data.

8. The inspection apparatus of a terminal fittings according to claim 7, wherein the image is a digital information, in which an optical power is indicated with a plurality of grades thereof, the extraction means compares the image of the terminal fittings, to which the electric wire is pressure-welded, picked up by the image pickup means and the plurality of the images in the image consulting data by a method of normalization correlation so that the image having the highest correlation value obtained by the method of normalization correlation out of the images is set up to be said most analogous image, and the judgment means judges the quality of the pressure-welding state of the electric wire to the terminal fittings mounted at the mount to be inspected to be good when the correlation value is equal to or higher than a predetermined threshold and the item symbol corresponding to the image of the terminal fittings picked up by the image pickup means corresponds, according to the normal data, to the proper item symbol for the mount to be inspected, and the judgment means judges the quality of the pressure-welding state to be no good when the correlation value is lower than the predetermined threshold or when the item symbol corresponding to the image of the terminal fittings picked up by the image pickup means does not, according to the normal data, correspond to the proper item symbol for the mount to be inspected.

9. An inspection apparatus of a terminal fittings for inspecting mounting state of the terminal fittings on an insulator and pressure-welding state of an electric wire, said terminal fittings being mounted at a mount to be inspected on the insulator and the electric wire being pressure-welded to the terminal fittings, the inspection apparatus comprising:

image pickup means for picking up an image of the terminal fittings mounted at the mount to be inspected on the insulator;

extraction means for (1) storing image consulting data including a plurality of item symbols wherein each of the item symbols corresponds to at least one of a plurality of images of non-defective terminal fittings mounted on the insulator, and storing normal data including a plurality of mounts to be inspected wherein each of the mounts to be inspected corresponds to at least one proper one of the item symbols, and for (2) comparing the image of the terminal fittings picked up by the image pickup means and the plurality of the images of non-defective terminal fittings in the image consulting data, and for (3) extracting an image most analogous to the image of the terminal fittings picked up by the image pickup means from the images in the image consulting data;

judgment means for judging the quality of the mounting state of the terminal fittings on the insulator in dependence upon the most analogous image, the image of the terminal fittings picked up by the image pickup means, the image consulting data, and the normal data;

second extraction means for (1) storing second image consulting data containing a plurality of images of a non-defective terminal fittings, to which the electric wire is pressure-welded, mounted on the insulator, and for (2) comparing the image of the terminal fittings, to which the electric wire is pressure-welded, picked up by the image pickup means and a plurality of images of a non-defective terminal fittings, to which the electric wire is pressure-welded, in the second image consulting data, and for (3) extracting an image most analogous to the image of the terminal fittings, to which the electric wire is pressure-welded, picked up by the image pickup means from the images in the second image consulting data; and second judgment means for judging the quality of the pressure-welding state of the electric wire to the terminal fittings, to which the electric wire is pressure-welded, mounted on the insulator by comparing the most analogous image and the image of the terminal fittings, to which the electric wire is pressure-welded, mounted on the insulator picked up by the image pickup means.

10. The inspection apparatus of a terminal fittings according to claim 9, wherein the image is a digital information, in which an optical power is indicated with a plurality of grades thereof, the extraction means compares the image of the terminal fittings picked up by the image pickup means and a plurality of the image in the image consulting data by a method of normalization correlation so that the image having the highest correlation value obtained by the method of normalization correlation out of the images is set up to be said most analogous image, the judgment means judges the quality of the mounting state of the terminal fittings on the insulator to be good when the correlation value is equal to or higher than a predetermined threshold and the item symbol corresponding to the image of the terminal fittings picked up by the image pickup means corresponds, according to the normal data, to the proper item symbol for the mount to be inspected, and the judgment means judges the quality of the mounting state to be no good when the correlation value is lower than the predetermined threshold or when the item symbol corresponding to the image of the terminal fittings picked up by the image pickup means does not, according to the normal data, correspond to the proper item symbol for the mount to be inspected, the second extraction means compares the image of the terminal fittings, to which the electric wire is pressure-welded, picked up by the image pickup means and a plurality of the images in the second image consulting data by a method of normalization correlation so that the image having the highest correlation value obtained by the method of normalization correlation out of the images is set up to be said most analogous image, and the second judgment means judges the quality of the pressure-welding state of the electric wire to the terminal fittings to be good when the correlation value is equal to or higher than a predetermined threshold while judges the quality of the pressure- welding state to be no good when the correlation value is lower than the predetermined threshold.

11. The inspection apparatus of a terminal fittings according to claim 5, 6, or 10, wherein the terminal fittings has a pressure-welding part to which the electric wire is pressure-welded and a caulking piece for caulking the electric wire, the image pickup means picks up at least one image out of an image of the pressure-welding part and that of the caulking piece, the image consulting data includes at least one plurality of images out of images of the pressure-welding part and those of the caulking piece, and the extraction means compares at least one image out of an image of the pressure-welding part and that of the caulking piece, which are picked up by the image pickup means, with at least one plurality of images out of images of the pressure-welding part and those of the caulking piece, which are included in the image consulting data.

12. The inspection apparatus of a terminal fittings according to claim 9, or 10, wherein the terminal fittings has a pressure-welding part to which the electric wire is pressure-welded and a caulking piece for caulking the electric wire, the image pickup means picks up at least one image out of an image of the pressure-welding part to which the electric wire was pressure-welded and that of the caulking piece which caulked the electric wire, the second image consulting data includes at least one plurality of images out of images of the pressure-welding part to which the electric wire was pressure-welded and those of the caulking piece which caulked the electric wire, and the extraction means compares at least one image out of an image of the pressure-welding part to which the electric wire was pressure-welded and that of the caulking piece which caulked the electric wire, which are picked up by the image pickup means, with at least one plurality of images out of images of the pressure-welding part to which the electric wire was pressure-welded and those of the caulking piece which caulked the electric wire, which are included in the second image consulting data.

13. The inspection apparatus of a terminal fittings according to claim 7 or 8, wherein the terminal fittings has a pressure-welding part to which the electric wire is pressure-welded and a caulking piece for caulking the electric wire,
   the image pickup means picks up at least one image out of an image of the pressure-welding part to which the electric wire was pressure-welded and that of the caulking piece which caulked the electric wire,
   the image consulting data includes at least one plurality of images out of images of the pressure-welding part to which the electric wire was pressure-welded and those of the caulking piece which caulked the electric wire, and
   the extraction means compares at least one image out of an image of the pressure-welding part to which the electric wire was pressure-welded and that of the caulking piece which caulked the electric wire, which are picked up by the image pickup means, with at least one plurality of images out of images of the pressure-welding part to which the electric wire was pressure-welded and those of the caulking piece which caulked the electric wire, which are included in the image consulting data.

* * * * *